United States Patent [19]
Spofford et al.

[11] Patent Number: 5,090,408
[45] Date of Patent: Feb. 25, 1992

[54] TRANSTRACHEAL CATHETER SYSTEM AND METHOD

[75] Inventors: Bryan T. Spofford, 1470 S. Quebec Way, #227; Kent L. Christopher, 9086 E. Colorado Cir., both of Denver, Colo. 80231; Michael E. Hovanes, Denver, Colo.

[73] Assignees: Bryan T. Spofford; Kent L. Christopher, both of Denver, Colo.

[21] Appl. No.: 101,172

[22] Filed: Sep. 28, 1987

Related U.S. Application Data

[63] Continuation-in-part of Ser. No. 788,817, Oct. 18, 1985, abandoned, which is a continuation-in-part of Ser. No. 673,912, Nov. 21, 1984, abandoned.

[51] Int. Cl.⁵ .............................................. A61M 16/00
[52] U.S. Cl. ............................ 128/207.14; 128/207.17
[58] Field of Search ......................... 127/207.14, 207.15, 127/207.17, 200.26, DIG. 26, 305.3; 604/117, 158, 272, 282, 283, 22, 264, 265

[56] References Cited

U.S. PATENT DOCUMENTS

| | | |
|---|---|---|
| 953,922 | 4/1910 | Rogers . |
| 2,210,744 | 8/1940 | Winder ............................ 128/207.15 |
| 2,868,199 | 1/1959 | Hudson . |
| 3,175,557 | 3/1965 | Hammond ....................... 128/207.14 |
| 3,538,918 | 11/1970 | Engelsher . |
| 3,682,166 | 8/1972 | Jacobs . |
| 3,688,774 | 9/1972 | Akiyama . |
| 3,788,326 | 1/1974 | Jacobs ............................. 128/707.15 |
| 3,874,377 | 4/1975 | Davidson . |
| 3,880,168 | 4/1975 | Berman . |
| 4,373,523 | 2/1983 | Treutelar ......................... 128/207.18 |
| 4,449,523 | 5/1984 | Szachowicz et al. ........... 128/200.26 |
| 4,483,337 | 11/1984 | Clair ................................ 128/207.17 |
| 4,488,545 | 12/1984 | Shen ................................ 128/200.26 |
| 4,502,482 | 3/1985 | DeLuccia et al. .............. 128/207.14 |
| 4,589,873 | 5/1986 | Schwartz et al. .................... 604/265 |
| 4,592,351 | 6/1986 | Smith et al. .................... 128/207.17 |
| 4,612,927 | 9/1986 | Kruger ............................ 128/200.26 |
| 4,669,463 | 6/1987 | McConnell ..................... 128/207.14 |
| 4,693,243 | 9/1987 | Buras .............................. 128/207.15 |

FOREIGN PATENT DOCUMENTS 2171017  8/1986  United Kingdom .

OTHER PUBLICATIONS

Heimlich et al., "Transtracheal Catheter Technique for Pulmonary Rehabilitation", 1985, pp. 502-504.
Heimlich, "Respiratory Rehabilitation with Transtracheal Oxygen System".

Primary Examiner—Kyle L. Howell
Assistant Examiner—John P. Lacyk
Attorney, Agent, or Firm—Dorr, Carson, Sloan & Peterson

[57] ABSTRACT

A system for continuously supplying supplemental therapeutic oxygen to a patient to enhance atmospheric breathing comprising an oxygen supply source for continuously supplying low pressure low volume oxygen to a patient at relatively low pressures and relatively low flow rates to supplement normal atmospheric breathing; flexible oxygen supply tube devices for supplying oxygen from said oxygen supply source to the patient; and a continuous one-piece constant diameter flexible elongated tracheal tube member having a continuous constant diameter passage extending therethrough and being flexible when inserted into an operative position within the trachea to provide therein an intermediate curved side wall portion extending between a proximate end side wall portion having an unrestricted inlet opening therein located posterior of the neck of a patient and a straight distal side wall portion located in the trachea and extending downwardly therein and having an unrestricted distal end outlet opening located in upwardly spaced relationship to the bronchial tubes of the patient.

35 Claims, 11 Drawing Sheets

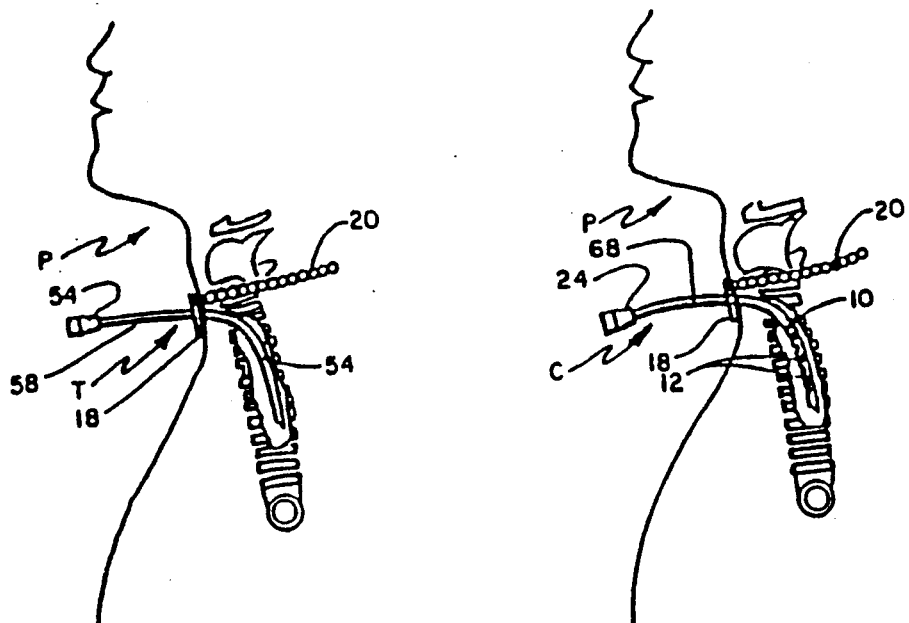
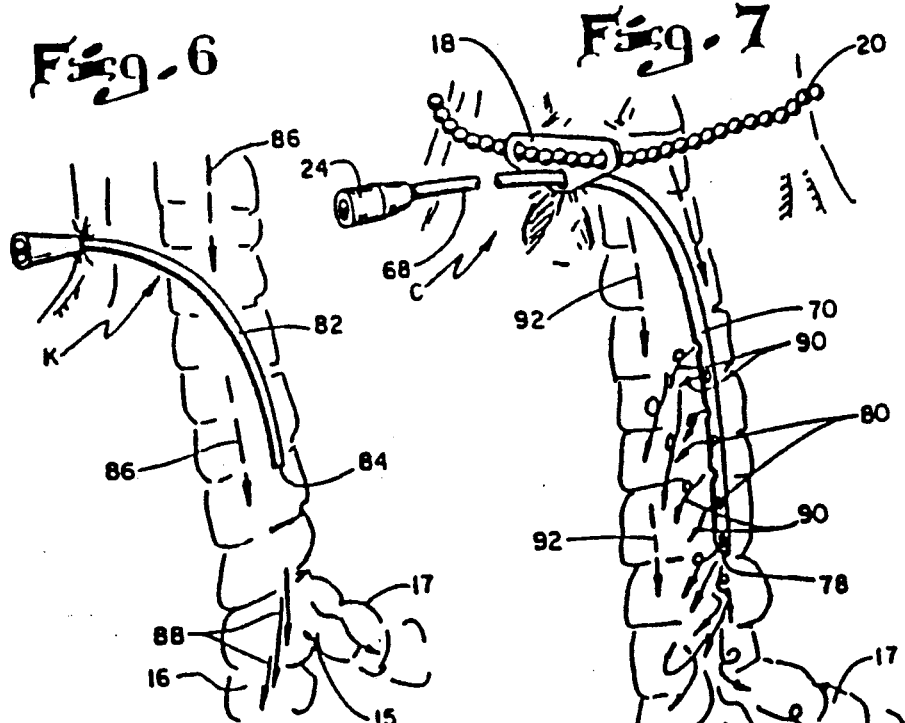

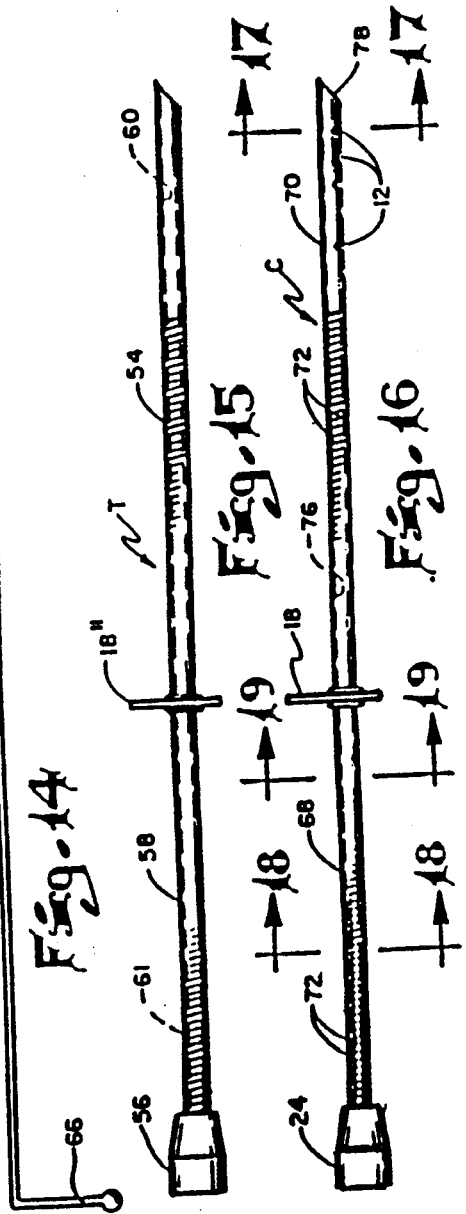

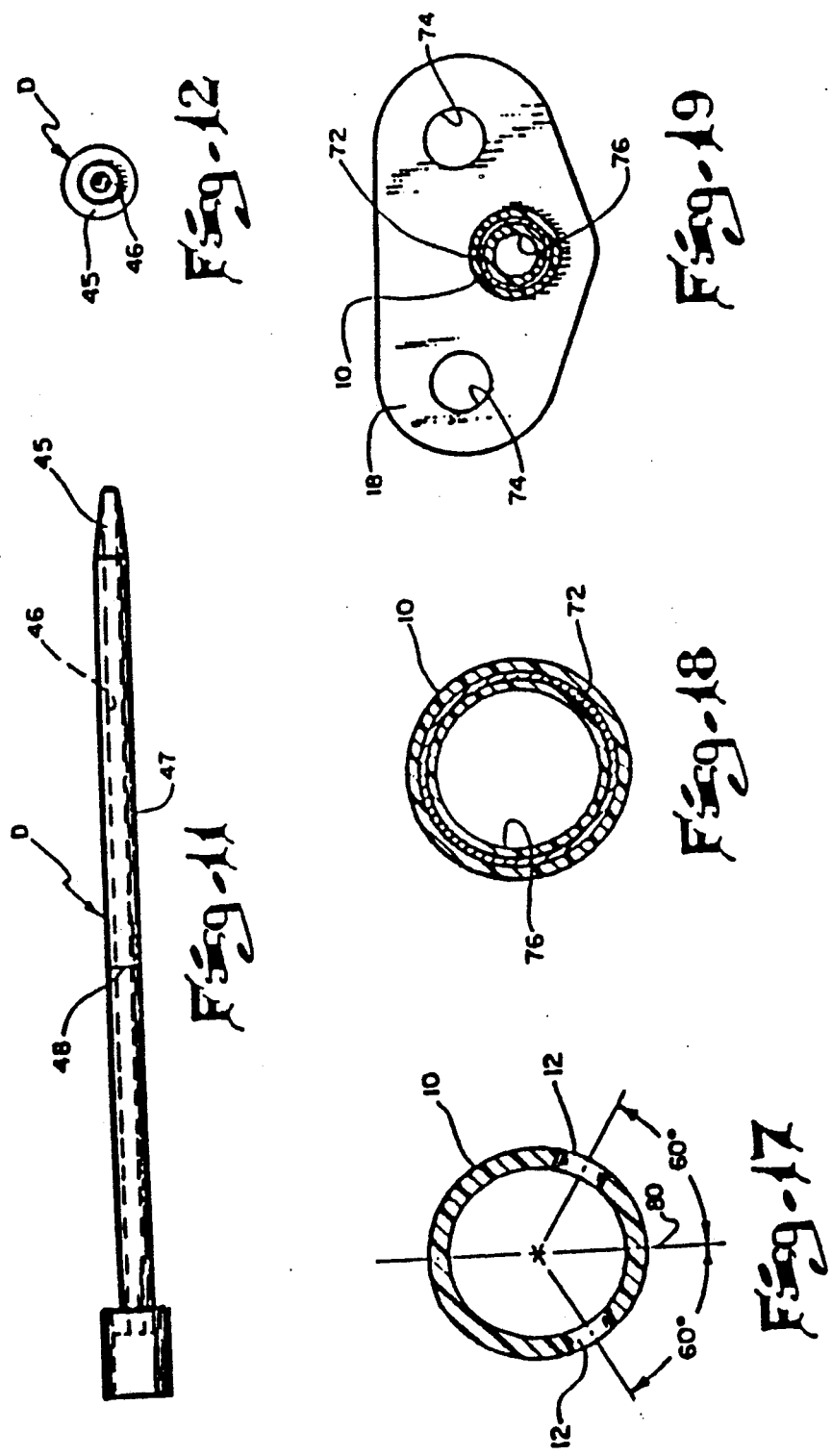

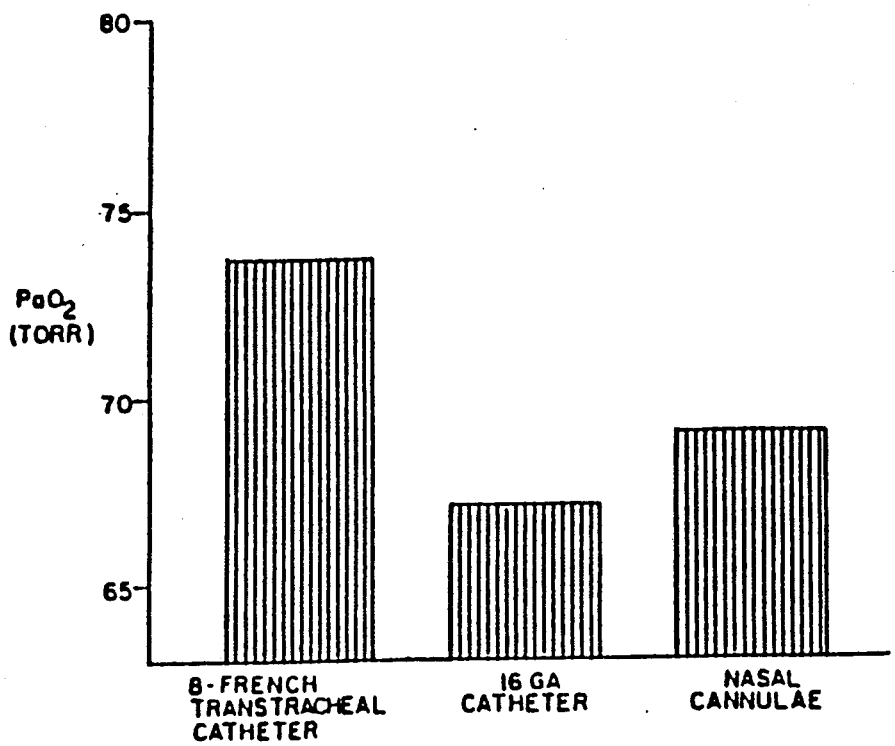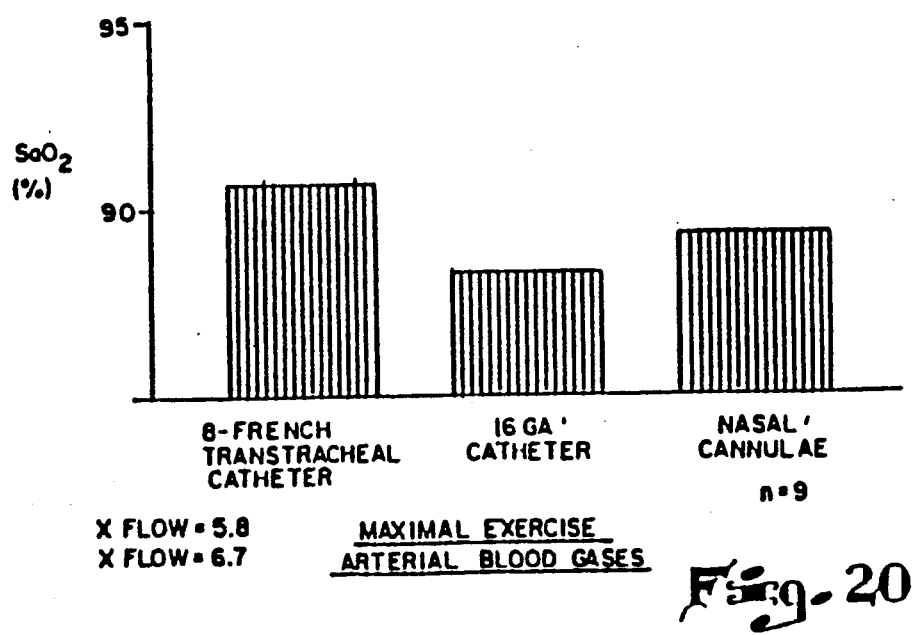
Fig. 20

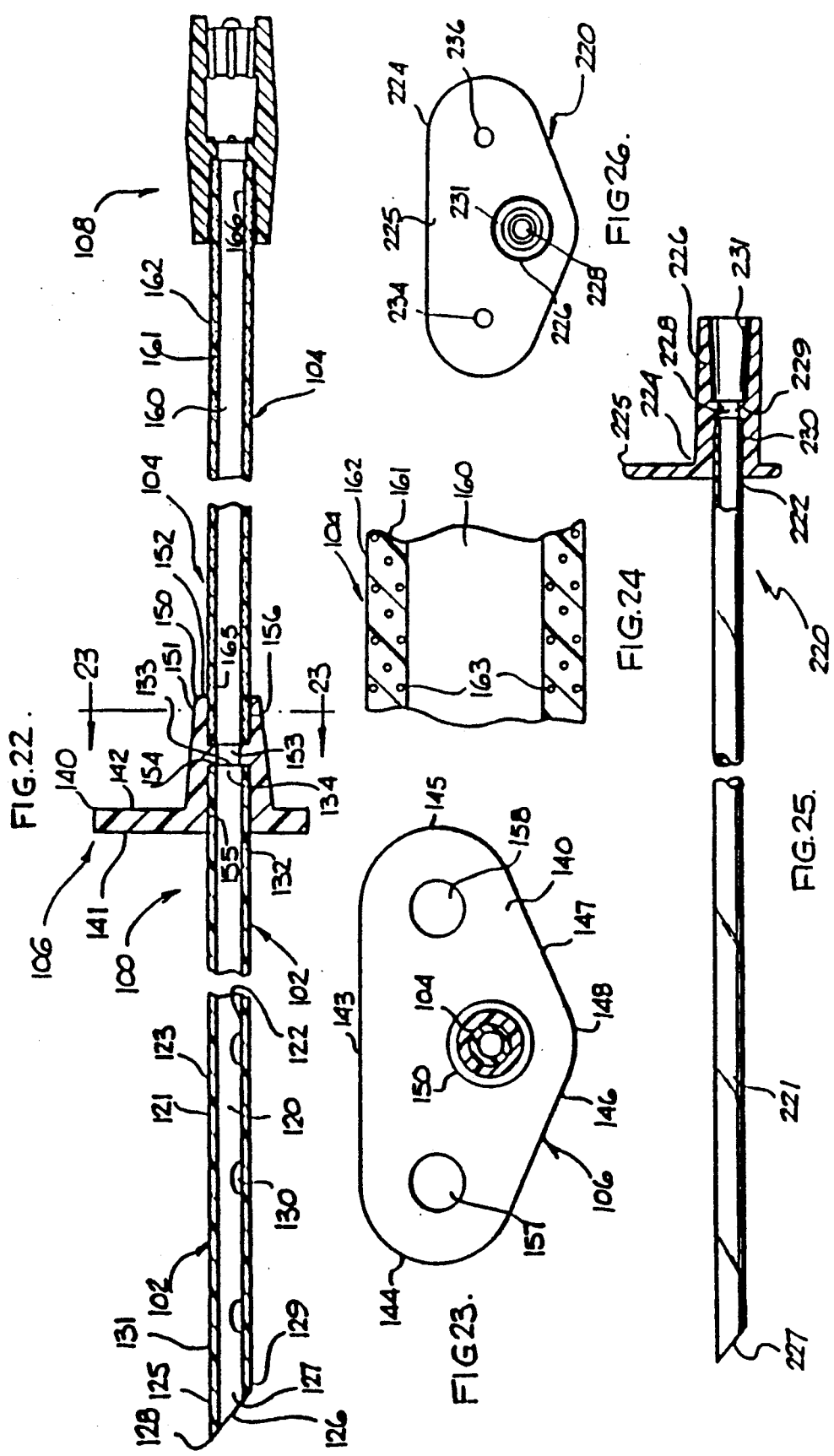

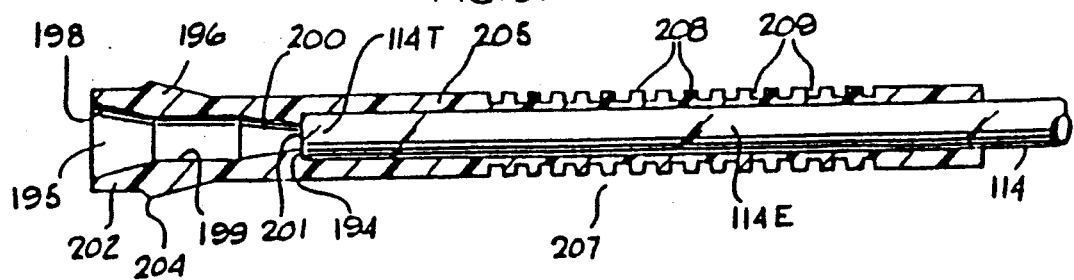
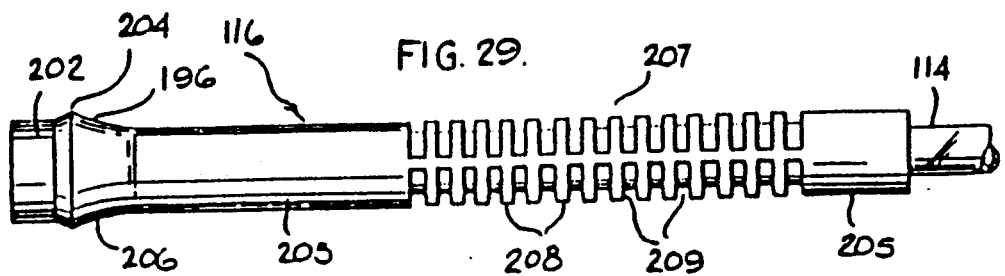
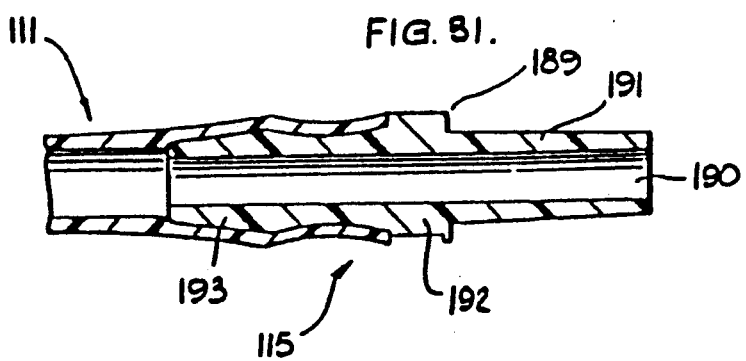

TRANSTRACHEAL CATHETER SYSTEM AND METHOD

This application is a continuation-in-part of copending U.S. Pat. Application, Ser. No. 788,817 filed Oct. 18, 1985, for TRANSTRACHEAL CATHETER SYSTEM AND METHOD, now abandoned, which is a continuation-in-part of U.S. Pat. Application, Ser. No. 673,912, filed Nov. 21, 1984, entitled "Transtracheal Catheter", now abandoned.

BACKGROUND OF THE INVENTION

1. Technical Field

This invention pertains to a system for supplemental transtracheal oxygen therapy including transtracheal catheter devices for providing transtracheal, oxygen delivery for spontaneously breathing patients with chronic lung disease and to methods for catheter placement and use. Such devices are medically desirable therapy for patients having a chronic need for oxygen where a catheter can be installed on an out-patient basis for permanent use.

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease (COPD). In other words, a patient's life and quality of life can be improved by providing a constant supplemental supply of oxygen to the patient's lungs.

However, with the current desire to contain medical costs, there is a growing concern that the additional cost of providing continuous oxygen therapy for chronic lung disease will create an excessive increase in the annual cost of oxygen therapy. Thus, it now desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Various other medical approaches which have been proposed to help reduce the cost of continuous oxygen therapy have been studied.

Various devices and methods have been devised for performing emergency cricothyroidotomies and for providing a tracheotomy tube so that a patient whose airway is otherwise blocked may continue to breath. Such devices, are generally intended only for use with a patient who is not breathing spontaneously and are not suitable for the long term treatment of chronic lung disease. Typically, such devices are installed by puncturing the skin to create a hole into the cricoid membrane of the larynx above the trachea into which a relatively large curved tracheotomy tube is inserted. As previously described, the use of such tubes has been restricted medically to emergency situations where the patient would otherwise suffocate due to the blockage of the airway. Such emergency tracheotomy tubes are not suitable for long term therapy after the airway blockage is removed.

Other devices which have been found satisfactory for emergency or ventilator use are described in U.S. Pat. No. 953,922 to Rogers; U.S. Pat. No. 2,873,742 to Shelden; U.S. Pat. No. 3,384,087 to Brummelkamp; U.S. Pat. No. 3,511,243 to Toy; U.S. Pat. No. 3,556,103 to Calhoun; U.S. Pat. No. 2,991,787 to Shelden, et al; U.S. Pat. No. 3,688,773 to Weiss; U.S. Pat. No. 3,817,250 to Weiss, et al.; and U.S. Pat. No. 3,916,903 to Pozzi.

Although tracheotomy tubes are satisfactory for their intended purpose, they are not intended for chronic usage by outpatients as a means for delivering supplemental oxygen to spontaneously breathing patients with chronic obstructive pulmonary disease (COPD). Such tracheotomy tubes are generally designed so as to provide the total air supply to the patient for a relatively short period of time. The tracheotomy tubes are generally of rigid or semi-rigid construction and of caliber ranging from 2.5 mm outside diameter in infants to 15 mm outside diameter in adults. They are normally inserted in an operating room as a surgical procedure or during emergency situations, through the crico-thyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. No. 3,682,166 and U.S. Pat. No. 3,788,326. The catheter described therein is placed over 14 or 16 gauge needle and inserted through the crico-thyroid membrane for supplying air or oxygen and vacuum on an emergency basis to restore the breathing of a non-breathing patient. The air or oxygen is supplied at 30 to 100 psi for inflation and deflation of the patient's lungs. The Jacobs catheter, like the other tracheotomy tubes previously used, is not suitable for long term outpatient use, and could not easily be adapted to such use.

Due to the limited functionality of tracheotomy tubes, transtracheal catheters have been proposed and used for long term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, Nov.–Dec. 1982; Respiratory Rehabilitation with Transtracheal Oxygen System) has been used by the insertion of a relatively large cutting needle (14 gauge) into the trachea at the mid-point between the crico-thyroid membrane and the sternal notch. This catheter size can supply oxygen up to about 3 liters per minute at low pressures, such as 2 psi which may be insufficient for patients who require higher flow rates. It does not, however, lend itself to outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an out patient basis. Such a feature is not only desirable but necessary for long term, out patient and home care use. Also, because of its structure, i.e. only one exit opening, the oxygen from the catheter is directed straight down the trachea toward the bifrucation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the carina, resulting in an undesirable tickling sensation and cough. In addition, in such devices, if a substantial portion of the oxygen is directed against the back wall of the trachea causing erosion of the mucosa in this area which may cause chapping and bleeding. Overall, because of the limited output from the device, it may not operate to supply sufficient supplemental oxygen when the patient is exercising or otherwise quite active or has severe disease.

Thus, none of the prior art devices are fully suitable for outpatient use on a long term basis.

It is therefore an objective of the present invention to provide a catheter, catheter insertion system and method for catheter insertion and use which will provide for efficient long term oxygen therapy, particularly for active patients.

DISCLOSURE OF THE INVENTION

The present invention provides an apparatus for supplying supplemental oxygen to a patient from a portable supply of oxygen which is capable of being carried by such patient, and which oxygen is capable of being introduced uniformly into both of the lungs of such patient on a continuous long term daily basis by conduction of supplemental oxygen into the cervical trachea (below the cricoid and above the sternal notch) through a transtracheal tube means unit including a intratracheal catheter portion disposed in the trachea in a downwardly extending position in the trachea with a distal end portion of such catheter, structured and located in the trachea sufficiently remote from the cricoid to permit adequate mixing of the oxygen introduced with the air from a spontaneously breathing patient. In one form of the invention, the transtracheal tube means unit comprises one continuous length of tubing, and in another presently preferred form comprises a separate intratracheal catheter member and a separate external oxygen supply tube member. The intratracheal catheter apparatus comprises an elongated flexible tube means having a durometer of from about 70 to about 90 Shore A and a length sufficient to locate the distal end portion inwardly within the trachea of the person above the carina; and to locate a proximate end portion outwardly of the neck for attachment of the proximate end portion to a tube connected to a portable supply of oxygen carried by the person; the intratracheal tube means having a lumen having a continuous smooth cylindrical outer peripheral surface and a continuous smooth constant diameter inner peripheral surface defining an elongated continuous cylindrical passage of constant outside diameter of between approximately 1.8 to 3.5 millimeters and being made of a flexible grade polymeric material having an inside diameter of between 1.7 and 3.0 millimeters; and oxygen outlet opening means at the distal end portion of the tubular means including a downwardly and anteriorly facing oval end opening, when said tube means is in place in the trachea, formed by a beveled end surface. The distal end portion of said tube means may also additionally contain a plurality of side wall openings located in predetermined spaced relationship above said end opening and extending through said sidewall and facing generally forwardly toward the anterior portion of the trachea for supplying oxygen only in a forwardly facing direction whereby rearward flow of oxygen toward the posterior portion of the trachea is limited to prevent erosion. The tube means may additionally contain reinforcement means mounted completely within said sidewall between said outer peripheral surface and said inner peripheral surface. In one form of the invention, the reinforcement means extends at least between said proximate end portion and said sidewall openings for maintaining a constant lumen cross-section in said tube means by resisting restriction of said central passage means in order to maintain said continuous constant diameter of said central passage means during oxygen therapy use. In the presently preferred form of the invention, the reinforcement means is located in the external oxygen supply tube member. The tube means may also be provided with hydrophilic coating means on the portion which resides inside the trachea and covering the cylindrical outer surface, and the cylindrical inner surface and the side and end opening surfaces for limiting adhesion and subsequent build-up of mucous-type materials present in the trachea which would otherwise restrict the flow of oxygen through said tube means. Thus the intratracheal catheter, as previously described, comprises a thin, flexible, kink and collapse resistant, tracheal tube means having a proximate end and a distal end which is fixedly attached to a flanged support means engageable with the patient neck and connected to an external oxygen supply tube means which may be an exterior portion of one continuous length of tubing or a separate outwardly extending tube member. A releasable connector means is attached to the outwardly extending proximate end of the external tube portion a sufficient distance so as to be capable of being viewed by the patient, so that the patient is better able to connect the external tube portion to a source of oxygen and to facilitate cleaning the catheter on an out-patient basis.

The invention also contemplates a method of inserting a transtracheal catheter in the trachea of a patient. The method comprises, under local anesthesia, the steps of infiltrating the soft tissue overlying the anterior side of the cervical trachea; advancing a hypodermic needle through the anesthetized tissue into the trachea; injecting local anesthetic into the trachea through the needle; inserting a guide wire through the needle; removing the needle over the guide wire; inserting a tissue dilator over the guide wire to enlarge the tract; removing the dilator; inserting a Stent over the guide wire and through the enlarged tract; removing the guide wire; securing the Stent by appropriate means, in place for a first period of time while initial healing of the dilated tract occurs so as to allow air to freely pass out through the lumen of the sterno rather than accumulating under the skin with the adherent risk of injury; removing the Stent; inserting a first catheter in the tract, which may be used on a temporary or longer-term basis, and securing the first catheter in place until the tract completely heals. Then, the first catheter may be removed and a second catheter may be inserted. This unique method allows the use of a small needle for the insertion of a catheter which is larger than the needle, but still capable of providing sufficient supplemental oxygen for oxygen therapy with active patients and not so large as to require a major surgical operation to insert. The first catheter is designed to enable cleaning in place by a cleaning rod with saline solution. The second catheter is designed to enable cleaning by removal by the patient.

The preferred apparatus for carrying out the foregoing procedure to create the tract can be provided in the form of a first kit. The first kit preferably includes a hypodermic needle for forming the small tract or fistula through the trachea and for use with a syringe for injecting an anesthetic into the trachea after the needle is inserted through the trachea to form the tract. The first kit also includes a guide wire for insertion through the needle to maintain the tract after the needle is removed. A dilator is provided, which is tapered and has a central passageway for threading it over the guide wire so that it can be used to gradually stretch the tissue to increase the diameter of the tract or opening. A Stent, having a central passageway is also provided in the kit and is inserted in the dilated tract after the dilator is removed in order to maintain the size of the tract or opening to facilitate initial healing of the tract. The guide wire is then removed. The Stent is held in position during healing by suturing.

A second kit or package includes the first catheter which has a single opening at a beveled distal end and replaces the Stent. The beveled end on the first catheter is longer on the posterior side so that the oxygen stream is directed away from the mucosa and toward the center of the trachea. This first catheter remains in place until the healing is complete and can be connected to a supply of oxygen during this period. A cleaning rod is also included in the second kit which is used periodically to clean out mucous which may form in the distal end of the catheter. To facilitate disconnecting and reconnecting the oxygen supply and the cleaning of the catheter, the proximate end of the catheter extends a sufficient distance outwardly from the surface of the tissue and the catheter holder so that the patient can see the connector thereon over his chin. Finally, a third kit or package includes a removable, second catheter which has similar dimensions as the first catheter and replaces the first catheter at the end of the tract healing period. The second catheter has a tapered distal end like the temporary catheter and also has a series of spaced openings in the anterior side wall thereof to facilitate mixing of the oxygen supplied through the tube with the air inhaled by the patient. These openings are spaced about an arc which does not exceed 60° from the mid-line on the anterior side of the tube.

The kits which have been described, together with the unique first and second catheters, provide the means for installing the catheters by a unique method. The catheters are suitable for out-patient use over extended periods of time by patients suffering from lung diseases causing hypoxia. The catheters can be cleaned by the patients, the second catheter being removable by the patient for cleaning and reinsertion. Because of the external extension of the proximate end of the tube beyond the connecting flange of the disclosed fastening means, the patient can see the connector and easily manipulate it to connect and disconnect the oxygen and instill drugs or other medications.

Additional advantages of the invention will become apparent from the description which follows, taken in conjunction with the accompanying drawings.

BRIEF DESCRIPTION OF THE DRAWINGS

FIG. 6 is a diagrammatical illustration of the insertion of a first transtracheal catheter after removal of the Stent;

FIG. 7 is a diagrammatical illustration of the insertion of a second catheter, after removal of the first catheter;

FIG. 8 is a diagrammatic view of the trachea with a flush-mounted prior art catheter showing the orientation of the catheter and the flow of oxygen to the patient from the catheter;

FIG. 9 is a diagrammatic view of the trachea, similar to FIG. 8, but showing the thorough mixing of oxygen and air by means of the catheter of this invention;

FIG. 10 is a side elevation of guide wire which forms a part of a first kit of this invention;

FIG. 11 is a side elevation of the dilator, which forms a part of the first kit of this invention, for use in the method of implanting the transtracheal catheter of this invention;

FIG. 12 is an end view of the distal end of the dilator of FIG. 11;

FIG. 13 is a side elevation of a Stent which forms a part of the first kit of this invention;

FIG. 14 is a side elevation of a cleaning rod which forms a part of a second kit of this invention;

FIG. 15 is a side elevation of a first catheter which forms a part of the second kit of this invention;

FIG. 16 is a side elevation of a removable, second catheter which forms a part of this invention;

FIG. 17 is an enlarged vertical section, taken along line 17—17 of FIG. 16, showing the angular spacing of the openings;

FIG. 18 is an enlarged vertical section, taken along line 18—18 of FIG. 16 showing the reinforcing means within the tubing;

FIG. 19 is an enlarged vertical section, taken along line 19—19 of FIG. 16 showing an attachment means for the transtracheal catheter FIG. 20 is a graph comparing oxygen therapy by an analysis of blood oxygen during exercise of the catheter of the present invention compared to other therapies;

FIG. 22 is a longitudinal cross-sectional view of the transtracheal unit shown in FIG. 1 prior to insertion into the trachea;

FIG. 23 is a transverse cross-sectional view of the transtracheal unit of FIG. 22 taken along line 23—23;

FIG. 24 is an enlarged longitudinal cross-sectional view of the external reinforced tube member of the transtracheal unit of FIG. 22;

FIG. 25 is a side elevational view partly in cross-section of a Stent;

FIG. 26 is an end view of the Stent of FIG. 25;

FIG. 29 is a longitudinal side elevational view of the oxygen tank connector member for the oxygen supply hose unit shown in FIG. 1;

FIG. 30 is a longitudinal cross-sectional view of the connection member of FIG. 29;

FIG. 31 is a side elevational view of the transtracheal unit connector member for the oxygen supply hose unit of FIG. 1.

DETAILED DESCRIPTION OF THE INVENTION

In General

Figure 1:
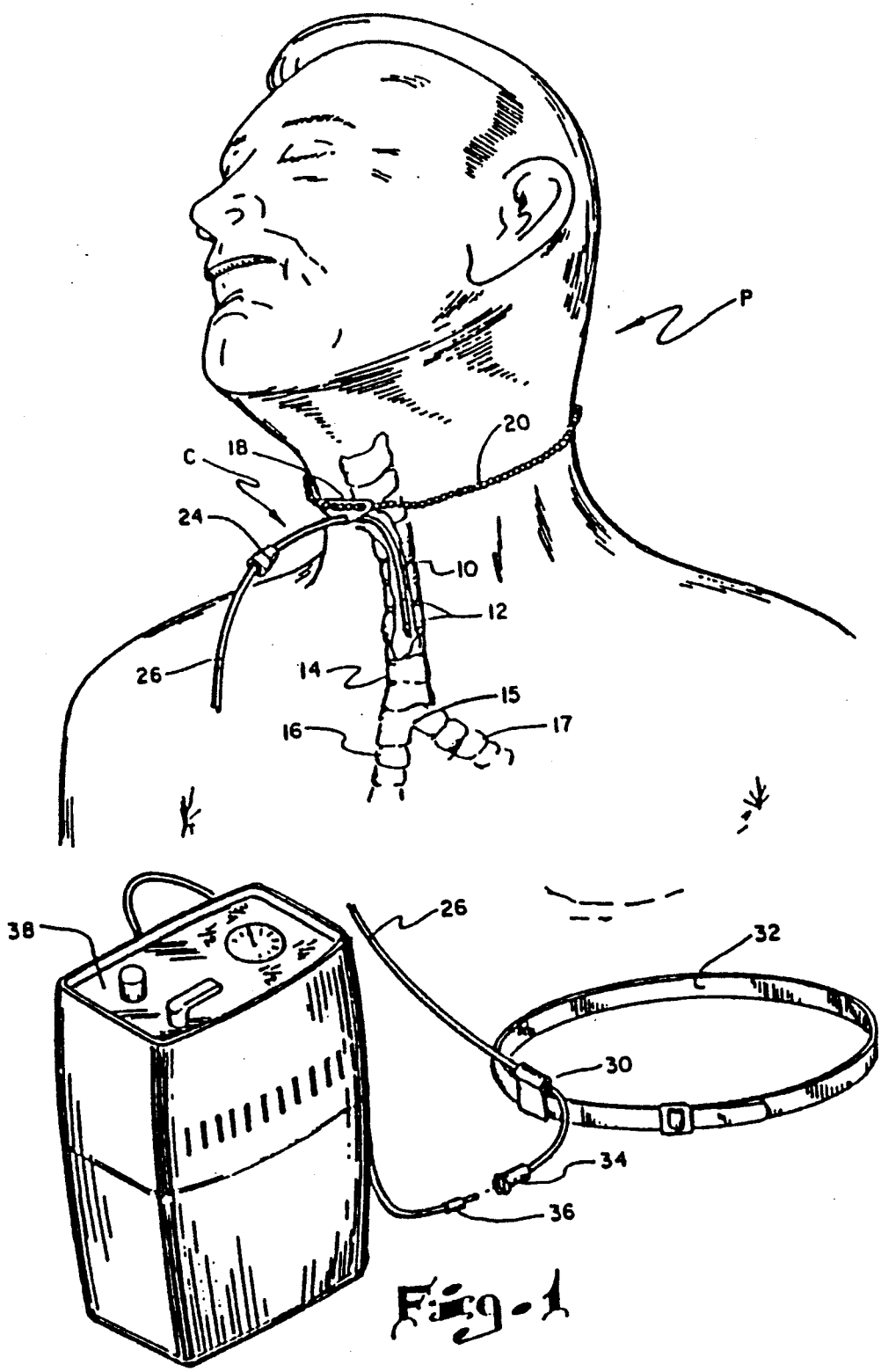
FIG. 1 is a perspective view showing the transtracheal catheter of this invention mounted through the skin and into the trachea of a patient and showing the oxygen supply connecting tube secured to the patient's wearing apparel between the connection to the transtracheal catheter and the connector to a supply of oxygen.

As best seen in FIG. 1, a patient P has been fitted with a transtracheal catheter C. In one form of the invention, the catheter includes a flexible tube 10 having a beveled distal end opening and may have a plurality of side wall openings 12 at the distal end thereof which have a specific orientation to facilitate the mixing of the oxygen with the air being breathed by the patient, as more fully explained hereinafter. The distal end, which extends through a tract in the trachea 14, is positioned above the carina 15 to supply the oxygen to the right and left bronchus 16 and 17. The catheter is inserted into the cervical trachea, in a manner more fully described hereinafter. After insertion, attachment means 18 is used to secure the catheter C to the patient's neck by means of a chain 20 extending around the patient's neck.

The proximate end of catheter C extends away from the patient's body and has a connector 24 attached to tube 10 through which oxygen is supplied to the patient. As is readily apparent, the extension provided, makes it possible for the patient to see connector 24 over his chin so as to connect and disconnect the oxygen supply tube and to even remove the catheter, as an outpatient, at home, for cleaning and then replace it and reconnect the oxygen supply. The source of oxygen can be from any source of oxygen such as pressurized oxygen tanks, liquid oxygen reservoirs or oxygen concentrators, with some variation in the prescribed flow rates.

As shown in FIG. 1, an intermediate reinforced tube 26 is provided which is connected between connector 24 through clip 30 which is shown on a narrow belt 32 that can be worn underneath the clothes of the patient P. However, the clip 30 can be attached directly to the patient's wearing apparel instead of using a supplemental belt. The connector 34 is then connected to tube 36 to oxygen supply 38. The purpose of this structure is to assure that as the patient moves about, the patient will not move to the limit of the tubing and place a stress on catheter C which could pull the catheter out of the trachea and perhaps cause injury or discomfort to the patient. With the intermediate tubing arrangement as shown, any tension would be placed on tube 36 and not on tube 26. In addition, the connector 24 is designed to disengage this also when subjected to a 1-3 pound pull.

The catheter system of the present invention ma include two catheters. The first is sometimes referred to herein as a temporary catheter which is used for a limited period of time while the tract or fistula formed through the trachea heals. The second catheter is sometimes referred to as the final catheter which is capable of being used by the patient on a long term basis but can be removed by the patient, at home, for cleaning on a periodic basis. However, it will be understood that the first catheter may also be used on a long-term basis without use of the second catheter. The differences in these catheters will be more fully explained hereinafter.

Both catheters are made of the same material and, with some differences, have the same dimensions. In this regard, for an adult patient, the catheter will have a length of approximately 20 cm and be made of polyurethane having a durometer between about 70 and about 90 Shore A (Shore 80 A being presently preferred) and a relatively small outside diameter (e.g., approximately between 1.8 and about 3.5 millimeters) such as to occupy only a small portion of the trachea without impeding normal spontaneous breathing of the patient. The attachment means 18 is located near the midpoint of the tube after placement and is approximately 7 to 11 cm (preferably 9 cm) from connector 24 on the proximate end of the tube and approximately 9 to 13 cm (preferably 11 cm) from the distal end of the tube when in place in the trachea. For an adult, the preferred diameter is an 8 or 9 French catheter. In some instances, it is contemplated that the outside diameter might be as small as 1.8 mm O.D. It is also contemplated that for pediatric patients the diameter might be as small as 1.5 to 2.0 mm O.D. Of course, the length would be correspondingly shorter to prevent the problems previously discussed.

Catheter Insertion Apparatus & Method

Figure 2:
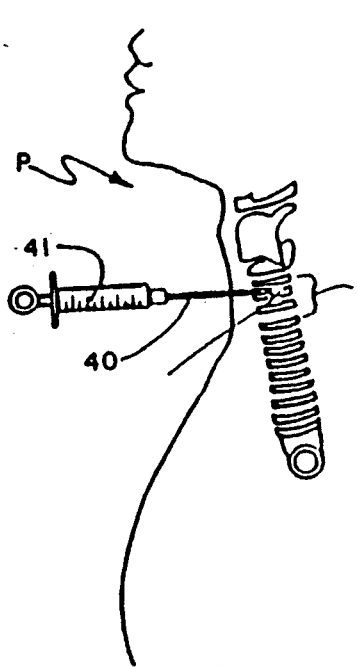
FIG. 2 is a diagrammatical illustration of the infiltration of a local anesthetic into the trachea by means of a needle on a syringe.

The method of inserting transtracheal catheter C is best illustrated in FIGS. 2-7. Conveniently, the method can be carried out by using apparatus contained in three kits. The first kit contains a hypodermic needle, a guide wire, a dilator and a Stent. The second kit contains the temporary catheter and a cleaning rod. A final catheter and a cleaning rod are contained in the third kit. In FIG. 2, a local anesthetic is injected into the soft tissues overlying the cervical trachea by means of a hypodermic needle 40 attached to a syringe 41 containing the anesthetic. Typically, a 5 cc syringe is filled with 1% lidocaine and epinephrine at a strength of 1:100,000. The needle may be 27 gauge×1.25 inches.

Figure 3:
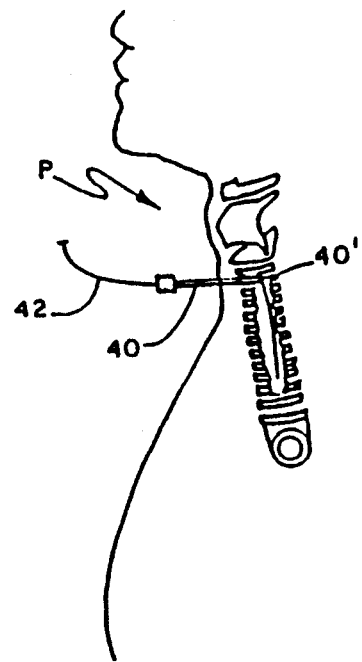
FIG. 3 is a diagrammatical illustration of the insertion of a guide wire through the needle after the syringe is removed.
Figure 4:
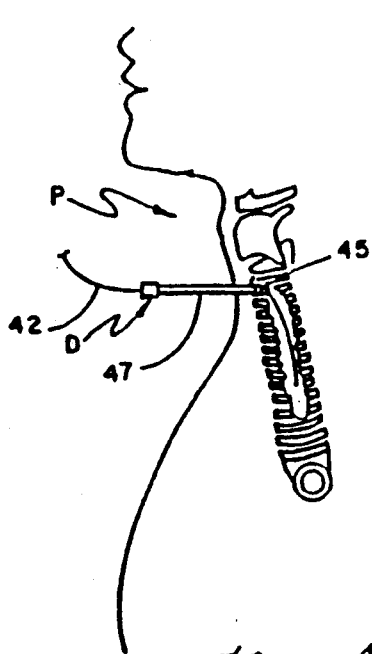
FIG. 4 is a diagrammatical illustration of the insertion of a tissue dilator over the guide wire after the needle is removed.

After local anesthesia is achieved in the skin, a No. 15 scalpel is used to cut just the skin. An 18 gauge thin wall needle, which is in the first kit, is attached to the syringe with the remainder of the anesthetic solution, and the needle is advanced into the trachea. Proper position may be documented by drawing back on the syringe and getting a return of air bubbles in the syringe. The remainder of the anesthetic is then deposited in the trachea. Because of the small size of the needle, the possibility of hemorrhaging is greatly reduced even though the tissue being penetrated is vascular. A 32 cm straight guide wire 42 is passed through the 18 gauge thin wall needle 40 into the trachea as seen in FIG. 3. The bevel on the needle and angle of insertion are exploited to direct the guide wire downwardly into the trachea. Conveniently, indicia, such as a notch is provided on the base of the needle to indicate the orientation of the bevel. The needle 40 is then removed over the guide wire.

As best seen in FIG. 10, guide wire 42 has an atraumatic end 43 which is designed not to scratch or otherwise injure the mucosa or trachea when the wire is inserted. This atraumatic end is preferably about 5 cm long. The wire includes a central longitudinal wire forming a core and a spirally wound wire around the core wire which core wire extends beyond one end of the spiral windings so as to form the flexible atraumatic end. The guide wire has a reference mark at about 11 cm from the atraumatic end to advise the physician on depth of insertion.

Next, preferably a 10 French by 15 cm long Teflon dilator D, found in the first kit, having a central bore 46 in the body 47 is passed over the guide wire 42 into the trachea. The initial small tract or fistula created by the hypodermic needle 40 is generally enlarged by the insertion of the taper of distal end 45 of the dilator into the tract. As the dilator is inserted no further than mark 48, see FIG. 11, the tract is stretched without cutting until it is enlarged sufficiently to receive the Stent. The tapered end 45 is preferably about 12 mm long. The dilator remains in place for at about one minute to accomplish sufficient stretching of the tissue.

Figure 5:
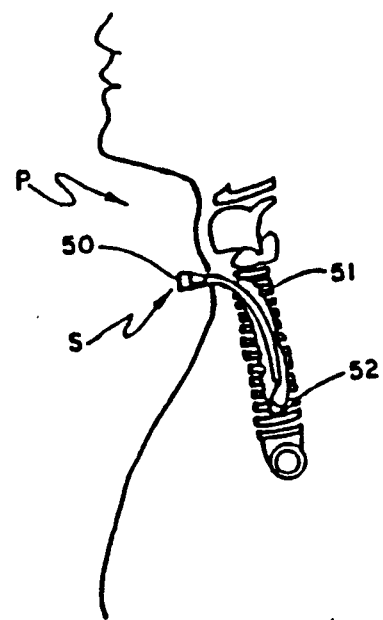
FIG. 5 is a diagrammatical illustration of the insertion of the Stent after the dilator and the guide wire have been removed.

Next the dilator is removed with the wire remaining in place and the Stent S is passed through the tract into the trachea over the wire, as best seen in FIG. 5. The structure of Stent S is illustrated in FIGS. 13.

The flange serves to stabilize the Stent by sutures placed through its eyelets and adapts to conventional Luer taper connectors for installation of lidocaine to suppress coughing. The Stent has a body 51 which is made of sufficiently rigid material to hold the tract which has been formed in the trachea open. This Stent body 51 has, preferably, a 9 French diameter and is preferably about 11 cm long from the distal tapered end 52 to the proximal end 50. The tapered end 52 facilitates insertion of Stent S through the tract in the trachea. A passageway 53 extends through the Stent to allow air to pass out without going under the skin to minimize the danger of the patient experiencing subcutaneous emphysema, during the process.

After typically one week, or longer if indicated, Stent S is removed by the physician and a temporary catheter T is inserted as shown in FIG. 6. One form of structure of this catheter is best seen by reference to FIG. 16. The temporary catheter is longer than the Stent, being about 20 cm in length. In fact, the length of the distal end 54 temporary catheter T which rests inside the trachea is approximately 11 cm long, which is the same length as the distal end of the Stent. The temporary catheter has a connector 56 at the proximate end 58 thereof for attachment to an oxygen supply. The extra length provided by proximate end 58 makes it possible for the patient to see connector 56 so that he can easily connect or disconnect the oxygen supply and can clean the catheter, as described below. This form of the catheter also has a longitudinal passageway 60 extending its entire length and may be provided with reinforcing means 61 which may take any form, but is illustrated as being in the form of a helical wire embedded within the tubular material that forms proximate end 58 and distal end 54 of temporary catheter T. The purpose of this armoring is to reduce the possibility of the catheter collapsing, or kinking from any manipulation done by the patient to thereby help assure a constant supply of oxygen to the patient by keeping a constant cross-sectional area in the catheter lumen. This is important since this device will be used by an outpatient who will not be under constant medical supervision. The distal end of lower portion 54 has a taper 62 which is longer on the posterior side to facilitate insertion and also to deflect the oxygen introduced through the catheter away from the mucosa at the back of the throat and to direct the oxygen downwardly and slightly forwardly. After proper positioning the temporary catheter T is connected to a source of oxygen. The oxygen flow is then adjusted to achieve a blood oxygen saturation of at least 90% by ear oximetry or arterial blood gas analysis.

Since oxygen is now being supplied to the patient through temporary catheter T, it is necessary to keep passageway or lumen 60 open. This is accomplished by use of a cleaning rod, such as cleaning rod R of FIG. 15. This form of cleaning rod is conveniently made of a flexible plastic and includes a long shaft 64 which terminates at its upper end in a handle 66 formed as a right angle extension from the shaft 64. Shaft 64 is slightly longer than the total length of the temporary catheter T. To clean out the catheter, the oxygen is disconnected and a saline solution is instilled through the passage, and then shaft 64 of cleaning rod R is inserted through connector 56 and along passageway 60. Because of the sizing, the length of shaft 64 is sufficient to completely expel any mucous which has accumulated within the passageway. Also, the diameter of shaft 64 is just slightly less than the inside diameter of passageway 58. This cleaning is normally done twice a day, or as often as needed. After cleaning, the cleaning rod R is removed and the connector 56 is reconnected to oxygen supply.

The temporary catheter is preferably kept in place for six weeks or longer so that the tract or fistula through the trachea can heal completely. After complete healing has occurred, the physician removes the temporary catheter T and provides the patient with a final catheter C which is inserted and positioned as shown in FIG. 7. This catheter is similar to the temporary catheter T with certain differences, as enumerated below.

Transtracheal Catheter Unit

The structure of one embodiment of the final transtracheal catheter C, which is a part of the third kit, is shown in FIGS. 16–19. The upper or proximate portion 68 of the catheter tube 10, as well as the lower portion 70, is also reinforced by means such as a coil spring 72 which is partially shown diagrammatically as embedded in the tubing (see FIG. 18). The purpose of this armoring is also intended to reduce the possibility of collapse or kinking of the transtracheal catheter which could restrict the oxygen supply to the patient. Conveniently, coil spring 72 extends a sufficient distance along the length of tube 10 to provide the described features with flange or fastening means 18 located at about 9 cm from the proximate connector 24 and about 11 cm from the distal tip. Each side of the fastening means has an aperture 74 (FIG. 19) for receiving a chain 20, or other holding means. The catheter tube 10 is provided with a longitudinal passageway or lumen 76 and the distal end has a taper 78 with a longer posterior side for directing the oxygen away from the mucosa of the trachea. A plurality of openings 12 are spaced about the anterior side of the catheter through an arc of approximately 120° and are all positioned on the portion of the sidewall which faces inwardly from the back wall of the trachea and are located above the shorter end of bevel 78'. In other words, the openings are spaced within 60° to either side of a mid-line 80 on the anterior side of the tube 10, as shown in FIG. 18.

The distinct advantage of this arrangement will be apparent from a viewing of FIGS. 8 and 9. In FIG. 8, a prior art catheter K is shown having a tubular body member 82 with a flat distal end 84 and no openings in the sidewall. As can be seen, most of the oxygen is directed straight downwardly in a stream into the right main stream bronchus 16 since it extends on a more straight downwardly path from the trachea than does the left bronchus 17. As a result air being drawn into the lungs of the patient by normal breathing, as shown by arrows 86, will be less likely to effectively mix with the stream of oxygen from the distal end 84 of catheter K as shown by arrows 88.

On the other hand, in one embodiment shown in FIG. 9, oxygen is discharged from catheter C through the beveled or tapered distal end 78 and openings 12 so as to be directed away from the mucosa at the back wall of the trachea and out into the body of the trachea as illustrated by arrows 90 to promote better mixing with the air from the patient's natural breathing, as indicated by arrows 92. This will occur because the oxygen is issued in multi-directional streams so that a substantial equal amount of oxygen enriched air passes essentially uniformly into both the right bronchus 16 and the left bronchus 17 and minimizes the drying effect of oxygen on the mucous membranes.

Another important distinction between the prior art catheter K and catheter C is that the connector of catheter K is flush against the trachea whereas the proximate end or extension 68 of catheter C extends outwardly for about 9 cm. This makes catheter C suitable for outpatient use, whereas catheter K is not. With extension 68, the patient can see connector 24 over his chin so that he can connect and disconnect the oxygen supply easily and can periodically remove the catheter for cleaning.

Oxygen is delivered at very low pressures, such as below 2 psi and at low flow rates, which are usually 50% or less than that which is required with a cannula. Of course, the catheter is only for use by a spontaneously breathing outpatient. Individuals who require more than 3 liters per minute transtracheal catheter either at rest or during exercise can receive up to 6-8 l/min. with the catheter of the present inventions. It can be seen from this chart that with the same flow rates in liters per minute for the 16 gauge catheter and the catheter of the present invention, blood oxygenation is improved for the described device. The nasal cannulae is clearly not as effective as the transtracheal catheters of the present invention even if operated at higher flow rates. Thus, a substantial savings can be obtained from reduced oxygen use while providing active patients with better blood gas values during the therapy. Used on a long term basis, this difference in efficiency should produce even more advantages to the patient in both the quality of life and extension of useful life.

From the foregoing, the advantages of this invention are readily apparent. A transtracheal catheter has been provided which is safe and comfortable for a spontaneously breathing patient and can be installed in a doctor's office on an outpatient basis without requiring hospitalization. A method of installation is provided whereby the transtracheal catheter is inserted under a local anesthetic, with the patient remaining ambulatory all times. Because of its small size, insertion can be accomplished with no risk of severing an artery. The transtracheal catheter is armored so that the possibility of kinking and crushing is minimized to assure a continuous supply of oxygen to the patient. Disconnection and reconnection of the oxygen supply is facilitated. The constant flow of low pressure oxygen into the collapsed airways of emphysema patients helps hold the bronchial tubes open to improve the function of the lungs and reduce the work of breathing.

The Kits

The above-described method is accomplished by the use of devices which are provided in a first, second and third kit. The first kit includes a needle for forming the initial tract in the trachea; an atraumatic guide wire which is fed through the needle to maintain the tract after the needle is removed a dilator slipped over the guide wire and used to enlarge the tract; and a Stent to replace the dilator to permit the tract to heal. A second kit is provided which includes a temporary catheter which replaces the Stent and remains in place for a period of several weeks while healing of the tract is completed; a cleaning rod for cleaning the temporary catheter; the third kit includes a removable, final catheter which replaces the temporary catheter after the healing is complete; and a cleaning rod.

An important feature of this method is that it allows a small catheter to be inserted by using an even smaller needle to form a tract which is subsequently dilated. The prior art, on the other hand, requires either a large tract for a smaller catheter or a large tract for a large catheter or tracheotomy tube to resuscitate a nonbreathing patient.

The first kit is an Insertion Tray that provides all the supplies less sterile gloves, Xylicaine, and facial tissue necessary to create a tract for the transtracheal catheters of the present invention. The paper drape around the tray may be opened to serve as a Mayo stand cover. The Insertion Tray has two tiers. The upper preparatory Tier should be used clean and provides the supplies for puncture site selection, local anesthesia and skin preparation. The Lower and second Procedure Tier should be used sterile and provides the supplies to create a catheter tract and stabilize the Stenting device.

The upper tier will preferably contain a surgical marking pen; 2—20" lengths of #3 stainless steel bead chain with connectors; disposable wire cutter; 3—alcohol prep pads; 5 cc Luer tip syringe; 27 ga×1.25" needle; 21 ga×1.5" needle; Hibiclens soap packet; prep well and sponge stick; and 2—4×4" gauze sponges to dry skin.

The lower tier will preferably contain a Steri-Drape (#1010); 2—4×4" gauze sponges; #15 Bard-Parker scalpel blade on disposable plastic handle; 18 gauge×7 cm thinwall needle; 5 cc Luer tip syringe; 32 cm×0.038" straight guide wire marked at 11 cm; 10 French×15 cm tissue dilator marked at 8 cm; Lubafax packet; 9 French Stent; Disposable needle holder and Disposable scissor; 3-0 Nylon suture 2 cm on FS-1 needle.

The Insertion Tray therefore provides all the supplies less sterile gloves and facial tissue necessary to create a tract for the transtracheal catheters. Most of the items included in the tray are commercially available and are gathered in an orderly sequence for the convenience of the physician.

| MANUFACTURERS OF INSERTION TRAY COMPONENTS | |
| --- | --- |
| Surgical Marking Pen | Devon Industries Chatsworth, CA 91311 |
| Stainless Steel bead chain | McMaster-Carr Chicago, IL 60680 |
| Scissor to cut bead chain #32048-022 | American Hospital Supply McGaw Park, IL 60085 |
| Alcohol Prep pads | The Kendall Company Hospital Products |

MANUFACTURERS OF INSERTION TRAY COMPONENTS

| | |
|---|---|
| 5 cc Luer taper syringe prefilled with 2% Xylocaine with epinephrine 1:100,000 | Boston, MA 02101 American Pharmaseal Laboratories Glendale, CA 91209 |
| Monoject 27 ga × 1.25" needle | Sherwood Medical St. Louis, MO 63103 |
| Hibiclens Soap | Stuart Pharmaceuticals Wilmington, DE |
| Sponge sticks | Johnson & Johnson New Brunswick, NJ 08903 |
| 4 × 4" gauze sponges | Johnson & Johnson New Brunswick, NJ 08903 |
| Steri-Drape #1010 | Surgical Products Division/3M |
| 4 × 4" gauze sponges | Johnson & Johnson New Brunswick, NJ 08903 |
| #15 Bard-Parker scalpel on disposable handle | Becton Dickinson & CO. Lincoln Park, NJ 07035 |
| 18 ga × 7 cm thin wall needle | Cook Inc. Bloomington, IN 47402 |
| 5 cc Luer taper syringe prefilled with 2 cc saline | American Pharmaseal Labs Glendale, CA 91209 |
| Lubafax packet | Burroughs Wellcome Co. Research Triangle Park, |
| Webster needle holder #32042-042 | American Hospital Supply McGaw Park, IL 60085 |
| Suture scissor | American Hospital Supply McGaw Park, IL 60085 |
| 3-0 Nylon suture on FS-1 needle | Ethicon Inc. Somerville, NJ 08876 |
| H-bandage | Johnson & Johnson New Brunswick, NJ 08903 |

The remaining apparatus is constructed as described, with biocompatible materials where necessary. For example, the temporary and permanent catheters are preferably constructed as described from medical grad polyurethane which may be coated as described with a hydrophilic polymer in the areas which are exposed, in use, to tracheal secretions. The polymer also provides a lubricious surface for each of insertion and removal. The polymer, also minimizes adherence of mucus to the catheter. Such polymers are currently used on other commercially available medical products such as feeding tubes which are in contact with mucosal surfaces for prolonged periods. The PVC material used in the security flange is preferably PVC or polyurethane material commonly used in medical devices which are in contact with the skin. It is soft and non-irritating. PVC and polyurethane can be securely bonded together.

The bevel of the tip of temporary and permanent catheters, and the side ports of the permanent catheter direct oxygen away from the tracheal mucosa toward the center of the air column in the trachea. This promotes patient comfort. Proper orientation can be facilitated by employing an asymmetric flange on the fastening means (see FIG. 9). Improper orientation may affect comfort but does not comprise efficacy.

The 9 cm extension of tubing from the flange to the female Luer-type taper connector removes the bulk of the connectors away from the collar. It also makes manipulation of the connectors easier for the patient. In addition, the pound release (range 1-3 pounds) of the female Luer-type taper connector is a feature which will result in a safety disconnect rather than catheter dislodgement in the event of an excessive pull on the proximal end of the Oxygen Hose.

The Cleaning Rod is designed to remove debris as it is passed through the lumen of either the temporary or permanent catheter. The length is preferably 5 mm longer than the catheter, and over-insertion or loss down the catheter is prevented by the 2 cm handle which is at a 90° angle and the small cap at the end of the handle.

Both, the temporary and permanent catheter of the present invention is most preferably an 8 or 9 French reinforced tube made of medical grade clear polyurethane with nylon coil spring reinforcement and approximately 20 cm (7.875") in length.

Procedures

Candidates for this procedure should demonstrate a need for chronic oxygen therapy with arterial blood gasses less than $PaO_2$ 55 Torr and an $SaO_2$ of less than 90% on room air during appropriate medical therapy. The use of transtracheal oxygen offers the patient greater mobility, improved cosmesis, and avoidance of nasal irritation by cannulae. Patients who are inadequately oxygenated with nasal cannulae or 16 guage transtracheal catheters may benefit from better oxygenation with the catheter of the present invention. The recommended pre-puncture evaluations should identify individuals for whom transtracheal oxygen therapy is contraindicated and others who require special considerations in the course of treatment.

The Puncture Technique uses an 18 gauge needle, wire guide and dilator to stretch an opening into the trachea with minimal discomfort. About one hour before the puncture, the patient is given is given oral prophylactic antibiotic with a sip of water. If not contraindicated, an oral narcotic is also administered for minor sedation and cough suppression. The patient removes his top and puts on a hospital gown. He is seated in a procedure chair with a head rest, and the head is elevated slightly to reproduce the position of the neck while looking in a mirror during catheter changes. Oxygen is continued throughout the procedure, but cannulae are repositioned so that they arrive from behind the head and do not interfere with the anterior neck. The Insertion Tray is removed from its plastic bag and placed on a Mayo stand at chest level in front of the patient. The paper wrapping is opened fully to act as a sterile drape for the Mayo stand. The superficial anatomy of the anterior neck is palpated carefully, and the notch of the thyroid cartilage, the crico-thyroid membrane and the notch of the manubrium are marked using the surgical marking pen. Visible anterior jugular veins should also be marked. A #3 stainless steel bead chain necklace is then placed around the patient's neck and trimmed with wire cutters to fit snugly but still accommodate two fingers. The chain is rolled down onto the trapezius muscles, and the intersection of the cervical trachea and necklace is marked for subsequent puncture. The highest acceptable puncture should be the tracheal interspace immediately below the cricoid cartilage (cricotracheal ligament), and the lowest should be the level of the manubrium. Occasionally a less snug necklace will be required to reach a low cricotracheal puncture site. A second length of bead chain is included for occasions when the first is cut too short. The customized chain is removed and placed in a labeled envelope for later use. The skin over the puncture site is prepared with an alcohol swab without removing the orientation marks. The 5 cc syringe is filled with 2% lidocaine with epinephrine 1:100,000 is attached to the 27 ga×1.25" needle. At the selected site, about 2 cc of this solution is infiltrated into the skin about 2 cm on either side of mid-line, and about 1 cc of local anesthetic is deposited into deeper pretracheal tissues. The needle is then exchanged for a 21 ga×1.5" needle. Facial tissue is given to the patient who is informed of an incipient cough, bad taste and globus sensation caused by the local anesthetic. The needle is passed transtracheally at the puncture site, and the remainder of local anesthetic quickly deposited onto the tracheal mucosa. A brief paroxysm of coughing may result. The anterior neck is prepared with Hibiclens soap using a sponge stick. Hibiclens soap is preferred to various iodophors because it is nonstaining and better suited for this outpatient procedure. The skin is then blotted dry with gauze so that the procedure drape will stick to the skin. The upper Preparatory Tier is now removed from the Mayo stand to expose the lower Procedure Tier which should remain sterile. Surgical gloves are now put on, and the Steri-Drape is applied to the upper chest at the level of the clavicles.

A 1 cm vertical incision centered at the puncture site is made with a #15 scalpel. Gauze sponge is held in the palm of the other hand while transfixing the trachea to maintain orientation. The incision should pass completely through the dermis into fat. Obvious anterior jugular veins should be avoided. The 18 ga needle, attached to the syringe containing saline, is then directed through the incision down to the trachea. Tracheal cartilages are palpated, and the needle is popped through an interspace. Air is aspirated into the syringe which is then removed. The notch on the hub of the needle is rotated until it is on the lower rim, and the tip of the needle is angled downward 45° toward the carina. The atraumatic end of the wire guide should pass freely into the lower airway. It is does not pass easily, the needle should be repositioned. The needle is withdrawn, and the 11 cm mark on the wire guide is positioned at the skin level. The 10 French dilator is then firmly advanced over the wire guide into the trachea but not more than the 8 cm. After one minute of stretching, the dilator is removed and exchanged for the 9 French Stent. Insertion of the Stent is facilitated by a small amount of water soluble jelly on its tip and constant twirling during gentle advancement. The wire guide is then removed.

The disposable needle holder and scissor are used to suture the Stent to the skin with 3-0 nylon suture. Sutures can be placed through each of 2 eyelets on a flange of the Stent taking care not to close the mid-line incision. The skin and lumen of the Stent should remain open to minimize the risk of subcutaneous emphysema. The H-bandage is then applied taking similar care not to create an occlusive dressing.

The patient is sent to the radiology department for posteroanterior and lateral chest X-rays to document catheter position and absence of pneumothorax and subcutaneous emphysema. Nasal cannulae oxygen is continued during the Stent week, and oxygen should not be administered through the Stent. Significant bleeding has not been observed because the method is relatively atraumatic. A nonfunctioning Stent is inserted in the newly formed tract for one week, and nasal cannulae oxygen is continued. Because the Stent functions as a drain, bacterial infection of the tract is not usually observed.

After one week of Stenting, the temporary transtracheal catheter is inserted by the physician over a wire guide, and transtracheal oxygen therapy is begun. The temporary catheter is designed to remain in place during the early week of transtracheal oxygen therapy when the tract is maturing. The catheter is cleaned in place using the Cleaning Rod and sterile saline. The kink and crush resistant Oxygen Hose adapts standard oxygen source to the catheter. Inadvertent decannulation is protected against by the suspender-type security clip which attaches to the top of the pants belt or dress and the 2 pound safety release of the Luer taper connector between the hose and the catheter.

In summary, the durometer values, i.e. about 70-90 Shore A, selected for the final configurations of the temporary and permanent catheters of the present invention are desirable and indeed necessary for proper insertion and long term patient comfort. In this regard, the spacing for the location of the holes of the distal end of the permanent catheter are preselected, within the range of orientation described, to retain a sufficient flexibility and stiffness to facilitate proper insertion, removal and cleaning, as well as enabling proper orientation, when in place, in order to achieve the benefits described herein. An 8 or 9 French size of the temporary and permanent catheters is the most preferred size since tests have shown that the proper back pressure, for a preselected range of oxygen flow rates can be achieved for this size of catheter to permit the efficient utilization of supplemental oxygen described herein.

PRESENTLY PREFERRED EMBODIMENTS

In a presently preferred form of the invention, as shown in FIGS. 21-31, a transtracheal catheter unit 100 comprises an intratracheal tube means 102, an external oxygen supply tube means 104, a connector-stabilizer-support means 106 with a releasable oxygen hose connector means 108. An oxygen supply hose unit 110 comprises a tube member 111, a non-releasable connector means 112, a clip means 113, a tube member 114, a connector means 115 fixedly attached to tube member 111 and a releasable coupling means 116 fixedly attached to tube member 114 which is releasably connectable to an oxygen supply source 118; such as a relatively small-size, small-volume (e.g. 0.6 to 1.1 liters of liquid oxygen) lightweight patient portable supply tank 117 capable of supplying ½ liter of gaseous oxygen for 10 to 12 hours through conventional valve flow control means or a relatively large-size, large-volume (e.g. 30 liters of liquid oxygen), heavy, stand alone-type, main supply cylinder or the like (not shown). Supply tank 117 may be carried by the patient in any suitable bag or pack device 118 having a shoulder or back strap 119.

As shown in FIGS. 22-24, the intratracheal tube means 102 comprises a continuous one-piece tubular member having an annular passage 120 defined by an annular wall portion 121 having an annular inner peripheral smooth surface 122 and an annular outer peripheral smooth surface 123. Distal end portion 125 has an inclined end surface 126 to provide an oval-shape discharge opening 127 extending between a lowermost tip portion 128 and an axially upwardly spaced portion 129. Tip portion 128 is preferably molded and polished for ease of insertion, comfort and avoidance of mucosal irritation. A plurality of forwardly facing side discharge openings 130 ma be provided in side wall portion 121 as previously described. A locator marking 131 may be provided on the upper side wall surface to promote recognition of partial withdrawal for repositioning without complete withdrawal. Proximate end portion 132 has a flat transverse end surface 133 defining a cylindrical inlet opening 134.

The intratracheal tube means 102 comprises a continuous, one-piece, tubular member made from a length of straight flexible thermoplastic tubular material such as polyurethane which easily conforms to the human anatomy to enable insertion into the trachea and has thermosetting characteristics so as to be able to adopt a flexible, thermoset, curved shape when subject to body temperature in continuous use in the trachea. Thus, a portion of the intratracheal tube member will gently rest against the posterior trachea wall in a stable position and will not move over corrugations of lateral and anterior tracheal walls with normal respiratory excursions while still maintaining a balance of overall flexibility for comfort. Intratracheal tube member 102 has a durometer of between approximately 70 to 90 Shore A (80 Shore A being presently preferred). Tube member 102 has an outside diameter of between approximately 1.8 millimeters to 3.5 millimeters (3.1 millimeters being presently preferred), but may be of smaller diameter (e.g. 1.5 to 2.7 mm) for pediatric patients. The inside diameter of tube member 102 is between approximately 1.7 to 3.0 mm (1.9 mm being presently preferred) so as to provide a minimum wall thickness of between approximately 0.1 to 0.9 mm (0.6 mm being presently preferred). The length of tube member 102 for adults is between approximately 8 cm to 14 cm (11 cm being presently preferred) so that distal tip portion 128 is located approximately 1 to 5 cm above the carina in a majority of adult patients. For pediatric patients, a length of 3 to 8 cm may be appropriate.

Connector-stabilizer-support means 106 is made of one piece of flexible molded plastic material such as clear PVC having a durometer of approximately between 51 to 61 Shore A (preferably 56 Shore A) which comprises a soft, flexible, relatively thin (e.g., approximately 0.72 inch) flange portion 140 having parallel flat, smooth side surfaces 141, 142. Flat inner surface 141 provides an abutment surface to engage the neck skin about the insertion tract. An upper flat peripheral surface 143 is connected by relatively large radius curved side peripheral surfaces 144, 145 to inclined lower peripheral surfaces 146, 147 which are connected by a relatively large radius curved lowermost peripheral surface 148. An outwardly extending hub portion 150 has a tapered outer peripheral surface 151 and terminates in a flat transverse side surface 152. A central bore 153 of approximately the same diameter (e.g., 0.72) as the inside diameter (e.g. 0.73) of tube member 102, is located in a transverse flange portion 154 between counterbores 155, 156 which are preferably tapered and have diameters approximately equal to or slightly less than the outside diameters of tube members 102, 104 so as to enable slidable, low-friction insertion of the ends of the tube members therewithin into abutting engagement with the side surfaces of flange portion 154. The end portions of the tube members 102, 104 are fixedly sealably attached to member 106 by any suitable means such as a solvent bond which is provided by applying a suitable solvent material to the outer periphery of each tubular portion prior to insertion into the counterbores. While it is intended that both tube members 102, 104 be permanently connected to member 106, the construction and arrangement is such that in the event of application of unusually large forces (e.g. 8 to 15 pounds), the bond between tube 104 and member 106 will break before the flange breaks away from the security necklace. Tube member 102 is precisely oriented relative to flange portion 140 so that the oxygen discharge opening in the tip portion 128 and side wall oxygen passages 130 will be properly located in the trachea whereby the oxygen is discharged forwardly. Flange portion 140 stabilizes the tube member 102, has a low profile and small surface area and is made of soft material for comfort and non-irritation in use while allowing the skin around the insertion tract in the neck to breathe. Flange portion 140 has circular openings 157, 158 for receiving a neck chain or band member 158 as previously described.

External tube means 104 is made of kink and crush-resistant molded plastic material such as polyurethane reinforced with braided nylon or polypropylene which resists cracking and breaking. Preferably, clear plastic material is used for cosmetics. Tube means 104 has a length of approximately between 2 to 12 cm (8 cm being presently preferred) so that connector member 108 is located a substantial distance beyond the connector-stabilizer-support member 106 to enable movement without displacement of the intratracheal tube member 102 and for comfort and ease of cleaning. Tube means 104 has a central cylindrical smooth-wall constant diameter passage 160 in an annular wall portion 161 having a cylindrical peripheral surface 162. Braided nylon material 163 is embedded in wall portion 161. End portions 165, 166 are permanently fixedly attached to flange member 106 and connector member 108, respectively. The diameter of passage 160 is approximately the same as the diameter of passage 120 in tube member 102 and passage 153 in flange portion 154 of member 106. In the presently preferred embodiment, tube member 104 has a durometer of approximately 80 Shore A, an outside diameter of approximately 3.0 mm and an inside diameter of approximately 1.7 mm.

Figure 27:
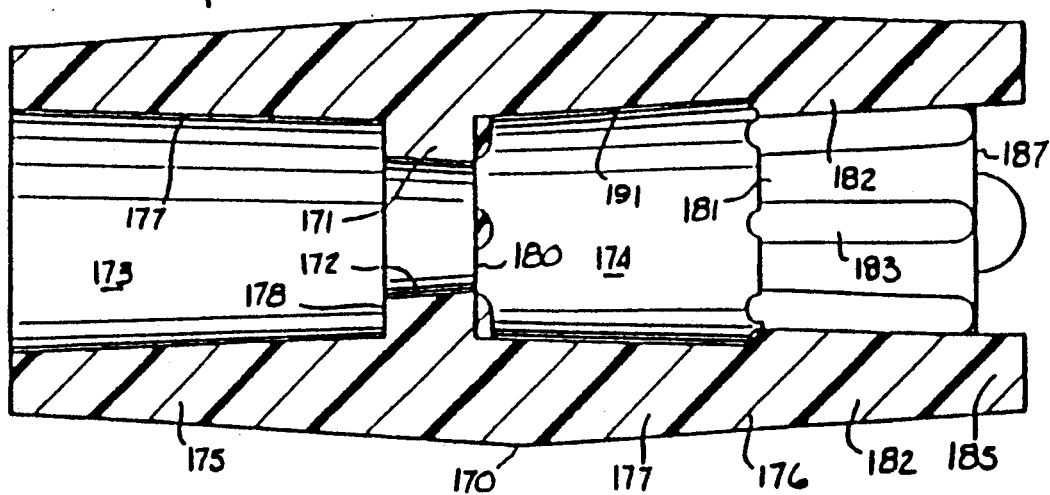
FIG. 27 is a longitudinal cross-sectional view of the connector member of the transtracheal unit of FIG. 22.
Figure 28:
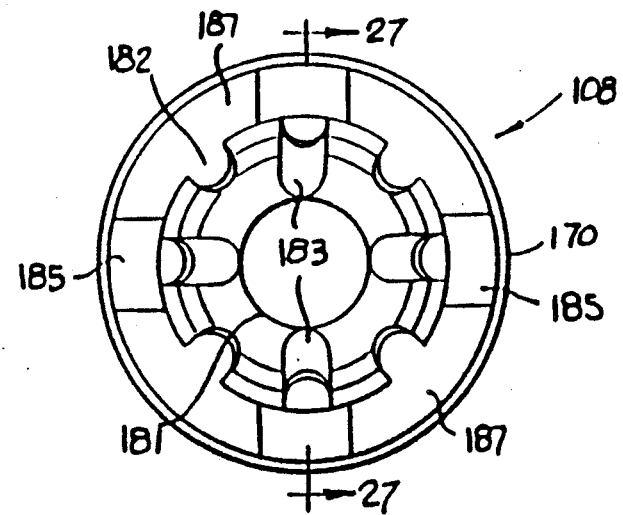
FIG. 28 is an end view of the connector member of FIG. 27.

Connector means 108, FIGS. 27 and 28, is of the same general construction as a conventional Luer compatible tapered oxygen friction connector device and is made of a one piece, generally cylindrical member 170 made of molded plastic material such as PVC having a durometer of approximately 51 to 61 Shore A (56 Shore A being presently preferred). Member 170 comprises a central rib portion 171 having a central, slightly tapered, generally cylindrical bore 172 extending between enlarged counterbore passage means 173, 174 in hub portions 175, 176. Counterbore 173 has a diameter approximately equal to the outside diameter of external tube member 104 and has a slightly outwardly tapered surface 177 so as to enable tube end portion 166 to be slidably inserted into engagement with annular side surface 178 of rib portion 171 and then permanently connected to connector 108 by suitable means such as a solvent bond as previously described. Passage means 174 comprises a central tapered conical passage portion 179 which terminates at radial shoulder portion 180 of rib portion 171 and an outer tapered conical passage portion 181 having circumferential space groove and rib portions 182, 183. Release tabs 185 are provided around transfer end surface 187. Connector means 115, FIG. 31, comprises a one piece connector member 189 made of rigid molded plastic material, such as polycarbonate or high density PVC, with a central cylindrical passage 190, a Luer-type tapered end portion 191, a central abutment flange portion 192, and a ribbed end portion 193 for fixed insertion into the end of tube member 111. In this manner, the elongated tapered connecting male portion 191 of connecting means 115 on the end portion of tubular member 111 is insertable into passage 174 of connector means 108 and securely releasably held therein with a retention force of approximately 1 to 5 pounds to provide a safety disconnect means while also enabling usage of standard medical devices, such as syringes and liquid capsules, to apply liquid medications or the like.

In the present preferred embodiment, oxygen supply tube member 111 is made of extruded plastic material, such as PVC having a durometer of between 45 to 60 Shore A (50 Shore A being presently preferred), with an outside diameter of approximately 3/16 inch and an inside diameter of approximately ⅛ inch and a length of approximately 20 inches. Oxygen supply tube member 114 is made of extruded plastic material, such as PVC having a durometer of between 65 to 75 Shore A (70 Shore A being presently preferred), with an outside diameter of approximately ¼ inch and an inside diameter of approximately ⅛ inch and length of about 50 inches. Tube members 111, 114 are permanently connected by connector member 112 by solvent bonding in aligned counterbores as previously described. Tube members 111, 114 preferably have the same inside diameters to prevent back pressure variances and have different outside diameters for maximum comfort along the body of the patient's inside clothing and maximum protection against collapse or kinking outside of clothing worn by the patient.

Figure 21:
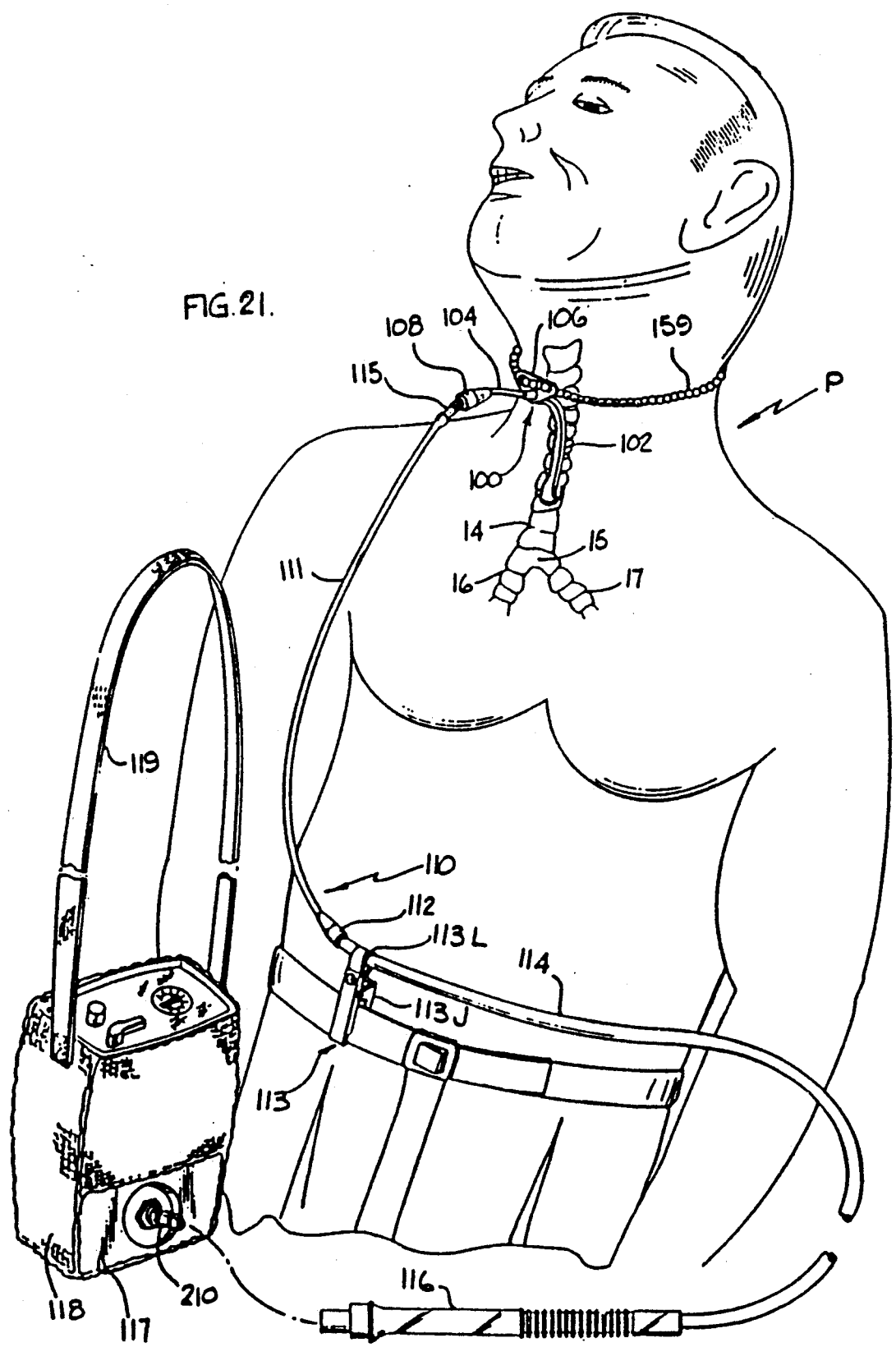
FIG. 21 is a perspective view of a presently preferred embodiment of the system, including a transtracheal unit and an oxygen supply hose unit in use with a patient.

Clip means 113, FIG. 21, comprises spring-biased openable and closable, pivotally-connected jaw members 113J, such as a suspender-type clip, with a plastic loop member 113L fixedly secured thereto and slidably adjustably frictionally mounted on tube member 114 adjacent connector 112 for attachment to a belt of any size.

Oxygen tank connector means 116, FIGS. 29 and 30, comprises an elongated body member of molded plastic material, such as clear PVC having a durometer of approximately 65 to 75 Shore A (70 Shore A being presently preferred), which is integrally fixedly molded around and bonded to end portion 114E of tube member 114 which terminates at 114T in abutting engagement with rib portion 194 adjacent a passage 195 in an enlarged end portion 196. Passage 195 comprises an outwardly tapered conical end portion 198, a central cylindrical portion 199, and an inwardly tapered conical end portion 200 terminating in a circular opening 201 in rib portion 194 and having a diameter approximately equal to the inside diameter of tube member 114. Head portion 196 has a cylindrical end portion 202 and an annular, outer rib portion 204 connected to an elongated tubular portion 205 by a conical surface 206. An intermediate portion 207 is provided with a series of rib and groove portions 208, 209 to enhance flexibility. Passage 195 is adapted to releasably receive an elongated ribbed male coupling portion 210, FIG. 21, on oxygen tank 117. The construction and arrangement of connector means 116 is such as to provide an elongated handle means to enable the user to firmly grip the connector means during connection and disconnection from the oxygen supply means without kinking of tube member 114. The tapered passage 195 facilitates connection to the oxygen supply hose and provides a reduced diameter transition to the supply hose inlet opening to minimize back pressure. The enlarged head portion prevents breakage and cracking of the wall portion.

FIGS. 25 and 26 shows a 9 French Stent device 220 which is generally similar to catheter unit portions 102 and 106 and comprises a one piece tubular member 221 having a proximate end portion 222 fixedly mounted in a one piece support member 224 which has a flange portion 225 and a hub portion 226. Tubular member 221 is made of flexible molded plastic material such as polyurethane having a durometer of between approximately 70 to 90 Shore A (preferably about 80 Shore A); an outside diameter of about 3.1 mm; an inside diameter of about 1.6 mm; and a beveled distal end surface 227 having an angle of inclination of about 35°. Support member 224 is made from one piece of molded plastic material such as PVC or polyurethane having a durometer of between approximately 70 to 90 Shore A (preferably about 80 Shore A). Hub portion 226 has a central tapered passage 228 in a central rib portion 229 connected to counterbore portions 230, 231. A proximate end portion 222 of tubular member 221 is fixedly mounted in counterbore 230 by solvent bonding as previously described. Counterbore portion 231 has a size and tapered shape to enable insertion of a standard size syringe. Relatively small-size openings 234, 236 in flange portion 225 enable suturing to the patient neck, but are smaller than the chain diameter to prevent use of the support chain 159 with Stent support member 224.

Figure 32:
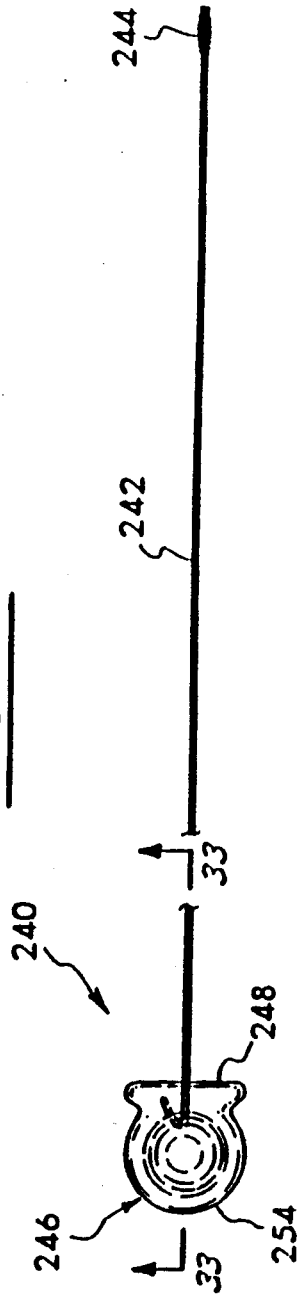
FIGS. 32 & 33 show a cleaning rod.
Figure 33:
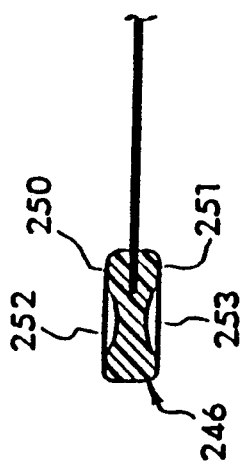

A presently preferred catheter cleaning rod 240, shown in FIGS. 32 and 33, comprises an 0.020 inch diameter stainless steel wire member 242 having a length of approximately 8.0 inches with an enlarged stainless steel atraumatic spring-stylet head portion 244 having an outside diameter approximately equal to the inside diameter of the tube. An injection molded plastic handle member 246, fixedly mounted on the other end of the wire, comprises a flat abutment surface 248 to prevent over-insertion of the wire beyond the tip of the catheter; a pair of flat side surfaces 250, 251 with indentations 252, 253 for gripping; and a rounded side surface 254.

Thus, the presently preferred embodiment of the invention provides a transtracheal catheter unit 100 having oxygen flow capability of from 0.1 to 8 liters per minute through an intratracheal tube member having an inside diameter of approximately 1.7 to 3.0 millimeters. The intratracheal tube member is made of flexible thermoplastic material having a durometer of approximately 70 to 90 Shore A and is capable of becoming set by body temperature in a curved position corresponding to the individual anatomy of the patient. Thus, the position and angle of the bend is variable for each individual patient while enabling usage of a cleaning rod within the oxygen passage in the intratracheal tube member. The construction and arrangement is such that the catheter tip rests against the smooth posterior wall portion of the trachea so as to reduce coughing which might result from location in the center of the trachea or in contact with the corrugated side or anterior wall portions of the trachea. The outside diameter is sufficiently small to permit unrestricted spontaneous breathing around the catheter. The catheter tip is beveled and positively oriented by the external connecting-locating flange so that the long axis of the oval opening faces forwardly to direct oxygen away from the tracheal mucosa to protect against drying and irritation. When relatively high flow rate oxygen (e.g. 2 to 8 liters per minute) is to be used, the side holes located near the tip portion further disperse the oxygen in a forward direction for comfort and to minimize drying. The oxygen passage is open to enable usage of a cleaning rod. The oxygen supply hoses and connector members provide for safety and ease of usage. The catheter-oxygen supply hose connector member provides a 1 to 5 pound force safety disconnect feature. The stabilizer member is connected to the tube members in a manner providing an 8 to 14 pound force safety separation feature. The large connector member at the end of the supply hose means provides an impedance matching feature while also being kink and crush resistant. The inside diameters of all tube members and passages in connecting members are approximately the same so as to provide a continuous substantially unrestricted constant passage between the tip portion of the intratracheal catheter and the source of oxygen.

In summary, the invention comprises a system for providing a continuous supplemental supply of relatively low pressure oxygen at a relatively low flow rate to enhance spontaneous breathing of a person having chronic hypoxemia. The system comprises a elongated intratracheal tube means having an elongated continuous constant diameter central passage means extending between an oxygen inlet opening means at a proximate end portion of the intratracheal tube means and an oxygen outlet opening means at a distal end portion thereof. The intratracheal tube means is fixedly permanently mounted on an external connector-stabilizer-support means for mounting on and support by the neck of a person and insertion into the trachea of the person through a surgically formed permanent insertion opening in the skin of the person located in the cervical trachea of the person. The external connector-stabilizer-mounting means is oriented relative to the intratracheal tube means for locating the distal end portion and the oxygen outlet opening means in the trachea below the cricoid cartilage and in upwardly spaced relationship to the carina. An external tubular means is fixedly connected to the connector-stabilizer-support means and has a length such as to provide a proximate end portion and oxygen inlet opening means located a sufficient distance away from the insertion opening in the skin to enable flexible displacement relative to the connector-stabilizer-support means without causing displacement of the intratracheal tubular means. The intratracheal tubular means is made of a continuous one-piece constant diameter flexible elongated intratracheal tube member having a continuous constant diameter passage extending therethrough and being flexible when inserted into the functional position within the trachea to provide therein an intermediate curved side wall portion extending between a proximate end side wall portion having an unrestricted inlet opening therein located outside of the neck of a patient and a substantially straight lowermost distal side wall portion located in the trachea and extending downwardly therein and having an unrestricted distal end outlet opening located in upwardly spaced relationship to the bronchial tubes of the patient. The intratracheal tube member has a relatively small outside diameter of between approximately 1.8 to 3.5 mm so as to be substantially less than the cross-sectional area of the patient trachea without substantially reducing the normal size continuous spontaneous breathing passage in the trachea to enable normal spontaneous breathing and has an inside diameter of no more than approximately 1.8 to 3.0 millimeters and a wall structure and thickness and a durometer of between approximately 70 to 90 Shore A such as to prevent collapse, kinking or other deformation causing restriction of oxygen flow and to enable continuous free flow of relatively low pressure relatively low flow rate oxygen therethrough from the inlet opening to the outlet opening with the pressure of the oxygen being no more than approximately 2 psi with flow rates up to 8 liters per minute. The connector-stabilizer-support means is connectable to neck support means for mounting around the neck of the person at a location between the larynx and the sternum and for holding the connector-stabilizer-support means proximate to the insertion opening in the skin. A frictional coupling means is provided on a proximate end portion of the external tube means for releasable connection to an oxygen supply tube means which comprises a first portion for mounting next adjacent the upper body of the person beneath clothing and having a disconnectable coupling means for releasable frictional coupling to the external tube means. The oxygen supply tube means further comprises a second portion with a coupling means for coupling to the oxygen supply source.

The distal end outlet opening on the intratracheal tube member has an inclined end surface and defines a longitudinally extending oval opening or slot means in a front portion of the distal side wall portion which faces toward the front side of the trachea of the patient for enabling only downward and forward flow of oxygen from the outlet opening and side facing slot means without rearward flow toward the rear side of the trachea.

A plurality of transverse laterally spaced forwardly facing oxygen outlet passage means may be provided in the distal side wall portion in upwardly spaced juxtaposition to the outlet opening and are located on only the forward half of the distal side wall portion facing outwardly toward the front side of the patient's trachea in a side wall area of no more than 180° circumference for enabling only forward and downward flow of oxygen toward the front of the trachea through the air outlet passage means without rearward flow toward the rear side of the trachea.

It is contemplated that the inventive concepts herein described may be variously otherwise embodied and it is intended that the appended claims be construed to include alternative embodiments of the invention except insofar as limited by the prior art.

What is claimed is:

1. A system for continuously supplying supplemental oxygen transtracheally from a portable oxygen source to supplement the spontaneous breathing of a patient suffering from chronic hypoxemia, said system comprising:

a transtracheal catheter having a subcutaneous portion and an exterior portion; said subcutaneous portion extending from said exterior portion a predetermined distance, said predetermined distance dependent upon a surgically formed opening located below the cricoid cartilage and above the manubrium of the cervical trachea in the neck of a patient for whom said system is to be used, to an area spaced above the carina in said patient;

(a) said exterior portion of said transtracheal catheter having a proximate end with means on said proximate end adapted to be connected to a portable oxygen source; said exterior portion further comprising means connected to said connecting means for extending said transtracheal catheter a sufficient length for said patient to (1) view said connecting means; (2) allow ease of manipulation of said connecting means; and (3) to move said connecting means away from a collar on an article of clothing worn by said patient;

(b) said subcutaneous portion of said transtracheal catheter providing a continuous flow rate up to about 8 liters per minute of oxygen from said portable oxygen source at a back pressure of less than about 2 psi; and (c) said subcutaneous portion of said transtracheal catheter being formed from a medically inert material having a durometer of between about 80 to about 90 Shore A, so as to have sufficient flexibility for long term use in said patient;

(d) said transtracheal catheter further comprising oxygen outlet means on a distal end portion of said subcutaneous portion for dispersing said oxygen uniformly into the right and left bronchus of said patient without interfering and blocking said spontaneous breathing of said patient;

means on said transtracheal catheter between said exterior portion and said subcutaneous portion adapted to locate said transtracheal catheter in position against said neck of said patient; and means slideably engaging said locating means on said transtracheal catheter adapted to secure said transtracheal catheter around said neck of said patient to hold said locating means against said neck thereby preventing accidental movement of said transtracheal catheter from said opening, said securing means being trimmed to have a length sufficient for said securing means to snugly fit against said neck at said formed opening.

2. The system of claim 1 wherein said subcutaneous portion of said transtracheal catheter has a continuous internal passageway and wherein said internal diameter is between about 1.7 mm and 2.5 mm.

3. The system of claim 1 wherein said extending means comprises forming said exterior portion of said transtracheal catheter outwardly from said locating means a length sufficient so said connecting means can be visibly seen by said patient over the chin of said patient so said connecting means can be easily manipulated and so said connecting means can be moved away from the collar of clothing worn by said patient, said extending means being formed from flexible material.

4. The system of claim 1 wherein said exterior portion further comprises means to resist kinking and collapsing of said transtracheal catheter.

5. The system of claim 4 wherein said transtracheal catheter comprises means imbedded within the sidewalls of said transtracheal catheter for reinforcing said sidewalls to resist kinking and collapsing of said catheter.

6. The system of claim 1 wherein said dispensing means further comprising means formed in said distal end portion to direct the flow of said oxygen away from the posterior walls of the trachea in order to minimize mucosal damage.

7. The system of claim 6 wherein said directing means comprise a beveled distal end having an elliptical end opening facing toward the anterior wall of said tracheal.

8. The system of claim 6 wherein said directing means comprise a plurality of openings formed in said distal end portion of said subcutaneous portion located longitudinally and peripherally between a 120 degree included angle on the anterior side of said subcutaneous portion.

9. The system of claim 8 wherein said directing means further comprise a beveled distal end having an elliptical end opening facing toward the anterior wall of said trachea.

10. The system of claim 1 wherein said system further comprises means to clean said transtracheal catheter while said transtracheal catheter is in place in said trachea.

11. The system of claim 10 wherein said cleaning means comprise a cleaning rod insertable by said patient through said transtracheal catheter to dispel mucus, said rod having a diameter slightly less than the internal diameter of said subcutaneous portion, a length greater than the length of said subcutaneous portion, and means on said rod preventing over extension of said rod in said transtracheal catheter.

12. The system of claim 1 wherein said subcutaneous portion comprising means to limit adhesion and subsequent build-up of mucus-like materials on the interior and exterior surfaces of said subcutaneous portion to prevent restriction of the flow of oxygen through said catheter.

13. The system of claim 12 wherein said limiting means comprise coating said interior and exterior surfaces of said subcutaneous portion with a hydrophilic material.

14. The system of claim 1 wherein said external oxygen supply is of a type to be easily carried by said patient during normal ambulatory activities.

15. The system of claim 1 wherein said portable oxygen source further comprises:
a portable oxygen tank,
means for selectively engaging said patient,
a first end of said reinforced tube slideably engaging said connecting means of said transtracheal catheter, the opposing end of said reinforced tube connecting to said portable oxygen tank,
means connected to said reinforced tube and to said engaging means for restricting movement of said reinforced tube so that movement by said patient minimizes stress on said transtracheal catheter, said first end of said reinforcement tube being further capable of selective disengagement from said connecting means when said stress exceeds about 1-3 pounds of pull.

16. The system of claim 1 wherein said flow rate means comprise forming said subcutaneous portion with a continuous internal passageway having an internal diameter of between about 1.7 mm and 3.0 mm.

17. The system of claim 1 wherein said subcutaneous portion formed from a medically inert material having a durometer of between about 70 to about 90 Shore A.

18. The system of claim 1 wherein said subcutaneous portion is formed form a material having thermosetting characteristics when continuously subjected to body temperature to form and maintain a shape according to the particular anatomy of said trachea and said neck of said patient.

19. The system of claim 1 wherein said subcutaneous portion and said exterior portions are separably secured to said locating means.

20. The system of claim 1 wherein said external oxygen supply comprises a portable oxygen supply easily transportable by said patient.

21. A system for continuously supplying supplemental oxygen transtracheally from a portable oxygen source to supplement the spontaneous breathing of a patient suffering from chronic hypoxemia, said system comprising:

a transtracheal catheter having a subcutaneous portion and an outwardly elongated exterior portion; said subcutaneous portion extending from said exterior portion a predetermined distance, said predetermined distance dependent upon a formed opening located below the cricoid cartilage and above the manubrium of the cervical trachea in the neck of a patient for whom said system is to be used, to an area spaced above the carina in said patient;
  (a) said elongated exterior portion of said transtracheal catheter having a proximate end with means on said proximate end adapted to be connected to a portable oxygen source; said exterior portion being formed to extend a sufficient length for said patient to view said connecting means over the chin of said patient to allow ease of manipulation of said connecting means and so said connecting means can be moved away from a collar on clothing worn by said patient;
  (b) said subcutaneous portion of said transtracheal catheter providing a continuous flow rate of oxygen up to about 8 liters/min from said portable oxygen source at a back pressure of less than about 2 psi; and
  (c) said subcutaneous portion of said transtracheal catheter being formed from a medically inert material having a sufficient durometer so as to maintain flexibility for long term use in said patient and an internal diameter in the range of about 1.7 mm to about 2.5 mm;
  (d) said transtracheal catheter further comprising at least one formed opening in a distal end portion of said subcutaneous portion for dispersing oxygen into the right and left bronchus of said patient without interfering and blocking said spontaneous breathing of said patient; and an internal diameter in the range of about 1.7 mm to about 2.5 mm;
means on said transtracheal catheter between said exterior portion and said subcutaneous portion adapted to locate said transtracheal catheter in position against said neck of said patient;
an attachment means engaging said locating means on said transtracheal catheter adapted to secure said transtracheal catheter around said neck of said patient to hold said locating means against said neck thereby preventing accidental movement of said transtracheal catheter from said opening, said attachment means being trimmed to have a length sufficient for said attachment means to snugly fit against said neck at said formed opening.

22. A system for continuously supplying supplemental oxygen transtracheally from a portable oxygen source to supplement the spontaneous breathing of a patient suffering from chronic hypoxemia, said portable oxygen source being carried by said patient, said system comprising:
  a transtracheal catheter having a subcutaneous portion and an exterior portion; said subcutaneous portion extending from said exterior portion a predetermined distance, said predetermined distance dependent upon a surgically formed opening located below the cricoid cartilage and above the manubrium of the cervical trachea in the neck of a patient for whom said system is to be used, to an area spaced above the carina in said patient;
  (a) said exterior portion of said transtracheal catheter having a proximate end with means on said proximate end adapted to be connected to a portable oxygen source; said exterior portion comprising an elongated flexible tube means connected to said connecting means for extending said transtracheal catheter a sufficient length for said patient to view said connecting means over the chin of said patient to allow ease of manipulation of said connecting means and to move said connecting means away from the collar of clothing worn by said patient;
  (b) said subcutaneous portion of said transtracheal catheter providing a continuous flow rate in a range to about 8 liters per minute of oxygen from said portable oxygen source at a back pressure of less than about 2 psi;
  (c) said subcutaneous portion of said transtracheal catheter having an internal diameter in the range of about 1.7 mm to about 2.5 mm;
  (d) said subcutaneous portion of said transtracheal catheter being formed from a medically inert material having a durometer of between about 80 to about 90 Shore A, so as to have sufficient rigidity for insertion and sufficient flexibility for long term use in said patient;
  (e) said transtracheal catheter further comprising oxygen outlet means on a distal end portion of said subcutaneous portion for dispersing said oxygen uniformly into the right and left bronchus of said patient by directing the flow of said oxygen away from the posterior wall of said trachea so as to minimize mucosal damage;
means on said transtracheal catheter between said exterior portion and said subcutaneous portion adapted to locate said transtracheal catheter in position against said neck of said patient;
a chain slideably engaging said locating means on said transtracheal catheter for securing said transtracheal catheter around said neck of said patient to hold said locating means against said neck of thereby preventing accidental movement of said transtracheal catheter from said opening, said chain being trimmed to have a length sufficient for said chain to snugly fit against said neck at said formed opening; and
means selectively engaging said transtracheal catheter for cleaning said transtracheal catheter by said patient while said transtracheal catheter is in said patient.

23. The system of claim 22 wherein said exterior portion further comprises means to resist kinking and collapsing of said transtracheal catheter.

24. The system of claim 23 wherein said transtracheal catheter comprises means imbedded within the sidewalls of said transtracheal catheter for reinforcing said sidewalls to resist kinking and collapsing of said catheter.

25. The system of claim 22 wherein said directing means comprises a beveled distal end having an elliptical end opening facing toward the anterior wall of said trachea.

26. The system of claim 22 wherein said directing means comprise a plurality of openings formed in said distal end portion of said subcutaneous portion located longitudinally and peripherally between a 120 degree included angle on the anterior side of said subcutaneous portion.

27. The system of claim 26 wherein said directing means further comprises a beveled distal end having an elliptical end opening facing toward the anterior wall of said trachea.

28. The system of claim 22 wherein said cleaning means comprises a cleaning rod insertable by said patient through said transtracheal catheter to dispel mucus, said rod having a diameter slightly less than the internal diameter of said subcutaneous portion, a length greater than the length of said subcutaneous portion, and means on said rod preventing over extension of said rod in said transtracheal catheter.

29. The system of claim 22 wherein said subcutaneous portion comprising means to limit adhesion and subsequent build-up of mucus-like materials on the interior and exterior surfaces of said subcutaneous portion to prevent restriction of the flow of oxygen through said catheter.

30. The system of claim 29 wherein said limiting means comprises coating said interior and exterior surfaces of said subcutaneous portion with a hydrophilic material.

31. The system of claim 22 wherein said portable oxygen source further comprises:
a portable oxygen tank,
engaging means for selectively engaging said patient,
a first end of said reinforced tube slideably engaging said connecting means of said transtracheal catheter, the opposing end of said reinforced tube connecting to said portable oxygen tank,
means connected to said reinforced tube and to said engaging means for restricting movement of said reinforced tube so that movement by said patient minimizes stress on said transtracheal catheter, said first end of said reinforcement tube being further capable of selective disengagement from said connecting means when said stress exceeds about 1-3 pounds of pull.

32. A system for continuously supplying supplemental oxygen transtracheally from a portable oxygen source to supplement the spontaneous breathing of a patient suffering from chronic hypoxemia, said system comprising:
a transtracheal catheter having a subcutaneous portion and an exterior portion; said subcutaneous portion extending from said exterior portion a predetermined distance, said predetermined distance dependent upon a surgically formed opening located below the cricoid cartilage and above the manubrium of the cervical trachea in the neck of a patient for whom said system is to be used, to an area spaced above the carina in said patient;
(a) said exterior portion of said transtracheal catheter having a proximate end with means on said proximate end adapted to be connected to a portable oxygen source;
(b) said subcutaneous portion of said transtracheal catheter providing a continuous flow rate to about 8 liters per minute of oxygen from said portable oxygen source at a back pressure of less than about 2 psi; and
(c) said subcutaneous portion of said transtracheal catheter being formed from a medically inert material having thermosetting characteristics when continuously subjected to body temperature to form and maintain a shape according to the particular anatomy of said trachea and said neck of said patient;
(d) said transtracheal catheter further comprising oxygen outlet means on a distal end portion of said subcutaneous portion for dispersing said oxygen uniformly into the right and left bronchus of said patient without interfering and blocking said spontaneous breathing of said patient;
means on said transtracheal catheter between said exterior portion and said subcutaneous portion adapted to locate said transtracheal catheter in position against said neck of said patient; and
means slideably engaging said locating means on said transtracheal catheter for securing said transtracheal catheter around said neck of said patient to hold said locating means against said neck thereby preventing accidental movement of said transtracheal catheter from said opening, said securing means being trimmed to have a length sufficient for said securing means to snugly fit against said neck at said formed opening.

33. The system of claim 32 wherein said exterior portion is formed to extend a sufficient length for said patient to view said connecting means over the chin of said patient to allow ease of manipulation of said connecting means and to allow said connecting means to be moved away from the collar of clothing worn by said patient; said elongated exterior portion (i) allowing periodic removal of said transtracheal catheter from said neck, (ii) allowing periodic cleaning of said transtracheal catheter while inserted and (iii) allowing periodic insertion and reconnection of said connection means to said portable oxygen source by said patient thereby making said transtracheal catheter suitable for long term outpatient use.

34. The system of claim 32 wherein said subcutaneous portion of said transtracheal catheter having an internal diameter in the range of about 1.7 mm to about 2.5 mm.

35. The system of claim 32 wherein said exterior portion further comprises means to resist kinking and collapsing of said transtracheal catheter.

* * * * *